(12) United States Patent
Fraser, Jr.

(10) Patent No.: US 9,707,257 B2
(45) Date of Patent: Jul. 18, 2017

(54) ANTI-HIV GROUP I INTRONS AND USES THEREOF IN TREATING HIV INFECTIONS

(75) Inventor: Malcolm James Fraser, Jr., Granger, IN (US)

(73) Assignee: The University of Notre Dame, Notre Dame, IN (US)

( * ) Notice: Subject to any disclaimer, the term of this patent is extended or adjusted under 35 U.S.C. 154(b) by 0 days.

(21) Appl. No.: 13/096,626

(22) Filed: Apr. 28, 2011

(65) Prior Publication Data
US 2012/0276071 A1 Nov. 1, 2012

(51) Int. Cl.
 C12N 15/113 (2010.01)
 C12N 15/12 (2006.01)
 C12N 15/11 (2006.01)
 A61K 35/545 (2015.01)

(52) U.S. Cl.
 CPC ........ *A61K 35/545* (2013.01); *C12N 15/1132* (2013.01); *C12N 2310/124* (2013.01); *C12N 2310/3519* (2013.01)

(58) Field of Classification Search
 None
 See application file for complete search history.

(56) References Cited

U.S. PATENT DOCUMENTS

2003/0095989 A1* 5/2003 Irving et al. ............... 424/233.1
2005/0222068 A1* 10/2005 Mourich ............. A61K 31/675
                                                       514/44 A

OTHER PUBLICATIONS

Kohler et al (J. Mol. Biol. (1999) 285, 1935-1950).*
Ryu et al (Molecular Therapy vol. 7, No. 3, Mar. 2003).*
Han et al (Virology 330 (2004) 221-232).*
Clontech product information for pLXRN (1/17/200).*
Miyoshi et al (Journal of Virology, Oct. 1998, p. 8150-5157 vol. 72, No. 10).*
Beerens and Berkhout (J. Virol. 76(5): 2329-2339, 2002).*
HIV-1/SIVcpz Complete Genomes; HIV Sequence Compendium 2011, retrieved from http://www.hiv.lanl.gov/content/sequence/HIV/COMPENDIUM/2011/hividna.pdf on Aug. 26, 2013.*
Beerens et al (J. Biol. Chem. 276(33): 31247-31256, 2001).*
Abbink Truus E, et al. 2004. J. Virol. 78(19), 10706-10714.
Allers K, HUtter G, et al. 2010. Blood Journal, doi: 10.1182/blood-2010-09-309591.
Ayre GB, Kohler U, et al. 1999. Proceedings of Nat. Acad. of Science. 96(7):3507-12. Mar. 30, 1999.
Bell M, Sinha J, et al. 2004. Biochemistry 43:4323-4331.
Blankson Joel N, et al. 2002. Annu. Rev. Med. 53, 557-593.
Byun J, Lan N, et al. 2003. RNA 9:1254-1263.
Carter J, Keith JH, et al. 2010. BMC Molecular Biology, 11:84
Cartier N, et. al. 2009. Science. vol. 326. Nov. 6, 2009.
Cate JH, Gooding AR, et al. 1996. Science. 273:(5282:1678-85. Sep. 20, 1996.
Cech TR. 1990. Annual Review of Biochemistry. 59:543-568.
Cowling V, and Downward J. 2002. Cell Death and Differentiation. 9:1046-1056.
Dobard Charles W, et al. 2007. J. Virol., 81)18), 10037-10046.
Freund F, Boulm F, et al. 2001. Antisense Nucleic Acid Drug Dev. 11(5):301-12. Oct. 2011.
Ghavami S, Hashemi M, Ande SR, et. al. 2009. J. Med. Genet. 46:497-51-. Jun. 7, 2009.
Hubner W, Chen P, et al. 2007. Journal of Virology. Doi10.1128/JVI.01088-07, 12596-12607. Nov. 2007.
Jung HS, Kwon BS, Lee SW, 205. Biotechnol Lett 27:567-574, (2005).
Jung HS, Lee SW, 2006. Biochem Biophys Res Commun 349:556-563.
Kastanos E, Hjiantoniou E, et al. 2004. Biochem Biophys Res Commun 322:930-934.
Kim A, Ban G, et al. 2007. Oligonucleotides 17:95-103.
Kohler U, Ayre BG, et al. 1999. J Mol Biol 285:1935-1950.
Kruger K, Grabowski PJ, et al. 1982. Cell 31:147-157.
Kwon BS, Jung HS, et al. 2005. Mol Ther 12:824-834.
Lamothe B, and Joshi S, 2000. Front. Biosci., 5, 527-555.
Lander ES, et al. 2001. Nature 409:860-921.
Li P, Nijhawan D, et. al. 1997. Cell 91:479-489. Nov. 14, 1997.
Willer B, Daecke J, et al. 2004. Journal of Virology, 10.1128/JVI.78.19.10803-10813.2004 p. 10803-10813. Oct. 2004.
Murphy FL, and Cech TR, 1993. Biochemistry. 32:5291-53—May, 1993.
Murphy FL, and Cech TR, 1994. Jour. Of Molecular Biology. 11:236, 49-63. Feb. 1994.
Nawtaison P, Keith J, et al. 2009. Virology Journal, 2009 6:73 (Jun. 4, 2009).
Potash Mj, Wei C, et al. 2005. PNAS 102:10; 3760-3765. Mar. 8, 2005.
Rossi John J. et al. 2007. Nat. Biotechnol., 25(12), 1444-1454. Dec. 2007.
Ryu KJ, Kim JH, Lee SW, 2003. Mol Ther 7:386-395.
Salvesen G, 2002. Cell Death and Differentiation. 9:3-5.
Salvesen G, and Dixit V. 1999. Proceedings of the National Academy of Sciences. Feb. 20-21, 1999.
Srinivasula S. Ahmad M, et al. 1998. Journal of Biological Chemistry. 273:17. Apr. 24, 1998.
Sullenger BA, Cech TR, 1994. Nature 371:619-622.
Waterston RH, et al. 2002. Nature 420:520-526. Dec. 5, 2002.
Won YS, Lee SW, 2007. J. Biotechnol 129:614-619. Feb. 14, 2005.

* cited by examiner

*Primary Examiner* — Richard Schnizer
(74) *Attorney, Agent, or Firm* — The Intellectual Property Law Office Verne A. Luckow, LLC

(57) ABSTRACT

Described is a unique class of antiviral molecule that can be applied to control and eliminate HIV infection in patients using myeloablation therapies and replenishment with transformed bone marrow stem cells programmed to express the antiviral molecule. These anti-viral molecules target the HIV genome in a highly conserved domain, and when expressed in cells prior to infection will cause the cell to die upon infection with HIV. Cell death insures no proliferation of new virus. Reconstituting the immune system with cells expressing these antivirals prevents re-establishment of HIV infection from reservoirs in the re-established lymphocyte and macrophage populations. Over time, reservoirs will be depleted entirely, effectively eliminating the virus. In effect, this new type of antiviral can be used to cure HIV infections.

24 Claims, 8 Drawing Sheets

PAS126 Sequence Alignment
Splice Junction at 142/143

```
                          \/
              130       140       150       160
Experimental  CTGTTGTGTGACTTGCATTCTGCATGGTCATAG
   Expected   CTGTTGTGTGACTTGCATTCTGCATGGTCATAG  (SEQ ID NO: 8)
```

PAS128W Sequence Alignment
Splice Junction at 144/145

```
                          \/
              130       140       150       160
Experimental  CTGTTGTGTGACTCTGGTTGGAACTCATGGTCAT
   Expected   CTGTTGTGTGACTCTGGTTGGAACTCATGGTCAT  (SEQ ID NO: 9)
```

PBS182W Sequence Alignment
Splice Junction at 198/199

```
                          \/
              190       200       210
Experimental  AAATCTCTAGCAGTGTCGTGACCACATGGTCAT
   Expected   AAATCTCTAGCAGTGTCGTGACCACATGGTCAT  (SEQ ID NO: 10)
```

LOOP128W Sequence Alignment
Splice Junction at 144/145

```
                          \/
              130       140       150       160
Experimental  CTGTTGTGTGACTCTGCTTGCCATT-CATGGTCA  (SEQ ID NO: 12)
   Expected   CTGTTGTGTGACTCTGCTTGGCATTGCATGGTCA  (SEQ ID NO: 11)
Differences                       *    *
```

FIG. 6

Target (Dual Loc): 867 bp
Intron: 367 bp
Splice Product: 319 bp

ANTI-HIV GROUP I INTRONS AND USES THEREOF IN TREATING HIV INFECTIONS

STATEMENT OF GOVERNMENT SUPPORT

The United States federal government owns rights in the present technology as research was supported by funds from National Institutes of Heath Grant #777.

INCORPORATION BY REFERENCE OF A SEQUENCE LISTING

The sequence listings contained in the files "761_191_007_US_3_ST25.txt", created on 2015 Jun. 29, modified on 2015 Jun. 29, file size 9,460 bytes, "761_191_007_US_2_ST25.txt", created on 2015 Mar. 26, modified on 2015 Mar. 26, file size 6,913 bytes, and "34341460.txt", created on 2011 Aug. 2, file size 2,073 bytes, are incorporated by reference in their entirety herein.

FIELD OF THE INVENTION

The present invention relates to the filed of pharmaceutical preparations and methods for treating and/or inhibiting human immunodeficiency virus (HIV) infection.

BACKGROUND OF THE INVENTION

At present there is no generally applicable cure for HIV infections of humans. While some development of anti-viral drugs and therapies exists, these have not yet proven capable of eliminating the virus from the infected patient. This is in large part due to the establishment of infected tissue reservoirs for the virus in which the virus may remain relatively quiescent for long periods of time, continuously shedding small amounts of virus into the patient to maintain or reestablish infection. A need continues to exist in the Art to cure a patient of the HIV infection.

While highly active anti-retroviral therapy (HAART) provides some suppression of HIV infection and allows restoration of immune function, effectively circumventing the decline into AIDS, HAART treatment alone cannot provide a cure for the infection. In addition, there remain several problems with this approach, including the expense of long term treatments, the continuing contagiousness of the patient, development of escape mutations, and toxicity associated with long term drug treatments. Discontinuation of HAART allows rapid rebound of the infection. Similarly, rebound of infection may occur through evolution and selection of quasi and mutated species resistant to HAART. Both of these viral rebounds result from an inability to completely clear the virus from infected patients due to the presence of persistently infected, long-lived lymphocyte or macrophage cell populations that serve as reservoirs for the virus (see Blankson et al., 2002).

Alternative approaches utilizing transplantation of ex vivo genetically transformed lymphocyte and macrophage lineage cells or progenitor stem cell populations are being explored as a means of suppressing HIV infection in susceptible cell populations (See Rossi et al., 2007). One major drawback to many of these approaches is their focus on suppressing the production of new virus in re-implanted cells while still allowing these cells to be re-infected. This approach allows the re-establishment and perpetuation of the very reservoirs that permit the evolution of quasi species of the virus, and allows escape mutants with these mutations to expand.

The first confirmed catalytic RNA, the cis-splicing intron of *T. thermophila* pre-rRNA, termed 'ribozyme' to describe the RIBO nucleic acid-based enzyme, was reported by Kruger et al. (1982). This intron excised itself from the highly purified mature rRNA in a solution of magnesium and guanosine in a cell-free system. Later, this intron was configured to splice together RNA on two separate molecules by two successive trans-esterification reactions (Sullenger & Chec, 1994).

The trans-splicing Group I intron reaction targets an RNA molecule through the use of antisense guide sequences that hybridize with the target RNA and permit cleavage at a specific uracil, releasing the downstream sequence (see FIG. 1). This step frees a 3' OH downstream of the uracil cleavage point to act as a nucleophile which carried out the covalent joining of the upstream target RNA fragment to an intron-associated 3' exon, resulting in a new, continuous RNA molecule. This reaction can be designed to generate a new contiguous open reading frame, leading to a transcript molecule that encodes a protein product that is present if and only if splicing has occurred.

In a trans-splicing reaction, two separate segments of the intron are utilized to specify the RNA sequence the ribozyme will target. The internal guide sequence and external guide sequence (IGS and EGS, respectively) are each complementary to a segment of the target. The IGS is limited in size to roughly 9 base pairs near the target uracil, and forms what is termed the P1 helix with the target, where the reaction will eventually occur. The EGS can be of nearly any length and forms a transient helix downstream of the target uracil. A longer EGS will increase the specificity and affinity of the intron towards its target RNA (Kohler et al., 1999).

The trans-splicing reaction is catalyzed by the P10 helix that is formed by the 3' end of the intron in the vicinity of the splicing reaction to guide the 3' exon to the proper ligation point. This step is vital to the second step of the reaction as it enables the free 3' OH of the cleavable uracil to attack the phosphate backbone upstream of the 3' exon, allowing covalent joining of the 3' exon to the upstream cleavage product to create a new, seamless mRNA suitable for translation.

Group I intron trans-splicing has been used in a number of applications including repair of mutant B-globin mRNA (Byun et al., 2003), restoration of wild-type p53 activity in three cancerous cell lines (Lander et al., 2001), re-establishment of the function of the canine skeletal muscle chloride channel (Waterson et al., 2002), and induction of p16 activity in a pancreatic cell line (Kastanos et al., 2004). The trans-splicing group I intron has proven to be an effective anti-cancer therapy in model systems. Researchers were able to cause the cell-specific death of human colon cancer cells by targeting an mRNA coding for the carcinoembryonic antigen utilizing HSV-tk as a 3' exon followed by ganciclovir treatment (Jung & Lee, 2006). This same group, using similar methods, achieved group I intron catalyzed trans-splicing of the liver-cancer upregulated α-fetoprotein (AFP) in human liver cancer cells (Won & Lee, 2007) and the mouse homologue of the cancer associated cytoskeleton-associated protein 2 in mammalian cells (Kim et al., 2007). Also reported is the cell-specific cytotoxicity induced via generation of diphtheria toxin A (DTA), or ganciclovir/ herpes simplex V thymidine kinase (HSV-tk)-induced apoptosis in cells expressing the tumo. These Group 1 trans-splicing introns r associated hTERT subunit of telomerase (Jung et al., 2005; Kwon et al., 2005), and trans-splicing of the hepatitis C virus internal ribosome entry site (HCV-IRES) (Ryu et al., 2003).

Despite these and other reports, a need continues to exist in the medical arts for more effective and long-lasting treatments for human immunodeficiency virus (HIV) infection, and in halting the progression of the infection to AIDS.

SUMMARY OF THE INVENTION

The present invention provides for methods and preparations that may be used in the treatment and control of human immunodeficiency virus infection, as well as the disease known as AIDS.

In one aspect, the invention provides for the use of specifically designed Group I trans-splicing introns that may be used as transgenic anti-viral (anti-HIV) agents. These agents effectively protect an animal against viral infection by human immunodeficiency virus using a "death-upon-infection" (DUI) approach. The effectiveness of this anti-viral strategy is demonstrated by the presently disclosed design of introns that attack conserved human immunodeficiency virus viral genomic RNA sequences. In particular, the present invention demonstrates the utility of these introns for the human pathogen, human immunodeficiency virus (HIV).

A unique class of anti-viral molecules is provided that may be used in clinical treatment methods to control and eliminate HIV infection in patients. In some embodiments, myeloblation therapies and replenishment with transformed stem cells programmed to express the antiviral (anti-human immunodeficiency virus) molecule is employed as part of the therapeutic method. By way of example, the transformed stem cells are transformed bone marrow cells. The antiviral molecules target the HIV genome in a highly conserved domain, and when expressed in cells prior to infection, will cause the cell to die upon infection with HIV. The death of HIV infected cells insures no proliferation of new virus will occur. As part of the treatment method, the patient will then be subjected to a treatment that provides for the reconstitution of the patient's immune system with cells expressing the antiviral molecules. The now reconstituted immune system of the patient thus prevents the re-establishment of HIV infection, such as re-infection that might otherwise occur from virus infected cells within reservoirs in the treated animal because of the re-established lymphocyte and macrophage populations. It is expected that over time, any reservoirs of infected cells will be depleted entirely, effectively eliminating the virus, thus providing a cure and/or method for inhibiting HIV infections.

A trans-splicing Group I intron approach is provided for suppression of HIV-infections in both humans and animals (e.g., mice, etc.), and presents an effective means of suppressing HIV infection.

The present invention is another aspect provides an ex-vivo transgenic procedure for treating infection by establishing modified (transformed) lymphocyte and macrophage stem cell populations that are incapable of supporting HIV infection in vivo, and providing the modified lymphocyte and/or macrophage stem cell populations to an infected individual/animal. In some embodiments, the lymphocyte and/or macrophage stem cell population is prepared from a population of cells obtained from the patient to be treated, and then transformed according to the present procedures prior to administration to the patient being treated.

In another aspect, the invention provides modified (transformed) lymphocyte and macrophage stem cell populations that are incapable of supporting HIV infection in vivo.

In yet another aspect, the invention provides Group I introns that attack HIV genomic or mRNAs, and that splice to these target RNA molecules a 3' exon encoding an apoptosis-inducing gene. HIV susceptible cells expressing this anti-HIV group I (αHIV-Grp1) intron will be effectively primed to undergo apoptotic cell death in response to infection by the HIV virus, rather than surviving and producing new progeny virus. This strategy will significantly reduce and/or eliminate, the possibility of generating escaping mutations. The effectiveness of this anti-HIV strategy may be verified in transformed cell cultures using splicing assays to demonstrate the activity of the αHIV-Grp1 intron, and virus titration assays to assess the productivity of the transformed cell cultures. Apoptosis assays may be used to verify the activity of the trans-spliced apoptosis-inducing product.

An in vivo animal model (mouse) will be used to demonstrate the utility of the present invention for providing a method and composition useful in the inhibition and/or treatment of an active HIV infection in vivo. This model permits examination of the parameters for application of this DUI strategy in vivo to eliminate HIV infection of a host, and ultimately cure the disease.

The present invention provides a means of suppressing HIV infections that will lead to an effective cure for this disease. By engineering target cell populations to undergo apoptotic cell death upon infection with HIV, instead of permitting the establishment of an infectious cell condition, the virus is divested of a means of re-amplifying in genetically modified, implant-derived tissues. Using procedures standard to the clinical field, patient-derived (autologous) bone marrow stem cells will be transformed ex vivo to express the presently disclosed anti-HIV effector gene. These transformed stem cells will then be re-implanted into the patient. The transformed stem cells will then expand in vivo with HAART suppression of the HIV infection. After sufficient expansion, removal of HAART and re-infection of these re-implanted cells would not result in re-establishment of the infection, but would result in a continual reduction of virus load through apoptotic death of these re-infected cells. Continued expansion of the remaining uninfected re-implanted cells eventually results in the replacement of susceptible cells and even reservoirs with virus free cells, thus curing the disease.

The utility of the present methods for providing a treatment for inhibiting and/or curing human immunodeficiency virus is supported in part by a study of a CCR5Δ32/Δ32 hematopoietic stem cell transplantation (SCT) to treat Acute Myeloid Leukemia in an HIV-1 infected patient (Allers et al., 2010). Following a protocol that involved depletion of the patient's own hematopoietic cells, the SCT resulted in replacement of patient hematopoietic cells with donor-derived lymphocyte and macrophage lineage cells, all CCR5Δ32/Δ32, and led to long term eradication of the HIV infection. However, this procedure does not provide for use of autologous cells, and requires finding a compatible donor that is CCR5 deficient. These drawbacks are eliminated with the present methods, which in certain embodiments provides for the use of autologous cells, and is not limited to the use of donor cells that are CCR5 deficient.

Using the Group I intron approach, the present invention provides a transgenic "death upon infection" strategy with a patient's own stem cells that will effectively accomplish long term suppression of HIV, and has the advantage of eliminating the necessity for finding a tissue compatible donor. Moreover, the Group I intron effector transgene can be coupled as a di-cistronic RNA molecule with an IRES dependent selectable gene that would permit selective expansion and maintenance of transformed SCT-derived cells, allowing expansion of transformed hematopoietic stem cells in vivo in the absence of immune ablation therapies.

Developing a cure for HIV infections is provided in one aspect of the invention. The successful demonstration of the effectiveness of this approach for suppressing chronic virus infections revolutionizes the treatment of several chronic infectious diseases. Analogous diseases that could be approached using this strategy are the chronic viral hepatitis diseases, HCV and HBV. In this sense the development of this transgenic anti-viral Group I intron approach provides a unique platform technology that provides for a new paradigm in the use of the presently described trans-splicing ribozymes in disease treatment.

The specific design of the present introns will include a conserved nucleotide sequence within the HIV genome, such as the sequence of the upstream $tRNA^{lys3}$ primer binding site (PBS) (Amarasinghe et al. (2000). The accessibility of conserved sequences to Group 1 intron attack within a specific 540 nucleotide long target sequence encompassing the 5' terminus of the HIV genome and including the tRNA PBS and Ψ-packaging signal was examined. The Ψ-packaging signal sequence was not useful as a targeted sequence for the Group 1 intron because the targeted sequence for cleavage occurred in a complex of the stem loop structure that was not accessible to intron under normal physiological conditions.

According to one aspect, an αHIV/Grp1 intron strategy is provided that targets absolutely or at least highly conserved sequences of the HIV genome that are present in the full length genomic RNA and in each mRNA molecule produced following proviral integration and expression. In this respect, another key innovation that is designed to insure success of the approach is the focus on the tRNA primer binding sequence as a relatively immutable and abundant target, thus insuring an extremely low probability, possibly none, of evolving escape mutants.

According to another aspect, an overall strategy of cell death upon infection as a means for reducing and eliminating virus from the infected individual is provided. The body does support and even encourages a reasonable amount of infected cell death because it ultimately results in lessened viral load. Effectively, the present methods and compositions provide an alternative means to cytotoxic T cell responses in ridding the body of infected cells.

In yet another aspect of the invention, the method for treating and/or inhibiting Human Immunodeficiency Virus (HIV) infection in an animal may be described as comprising: transfecting an autologous stem cell sample from a patient in need of treatment with the retroviral vector of claim 2 to provide a population of cells comprising transformed autologous cells that constituitively express a selected αHIV-Group 1 trans-splicing intron; and administering said transformed autologous stem cells to the animal to provide a treated animal, wherein transformed autologous stem cells and cells derived therefrom that become infected with Human Immunodeficiency virus in the treated animal will undergo apoptotic cell death. In some embodiments, the transformed autologous stem cells comprise reconstituted susceptible cells with a targeted trans-splicing molecule that generates apoptotic cell death in the presence of HIV mRNA. In the presence of the transformed population of stem cells, the ability of the HIV virus to re-establish infection in the treated animal is eliminated. In some embodiments, the animal is a human.

In some embodiments of the method, the patient/animal may also undergo a supplementary immune ablation treatment prior to receiving the transformed autologous stem cells. In other embodiments, the patient/animal may further be treated with a step of receiving a highly active retroviral treatment (HAART), such as to augment suppression of the HIV infection. The autologous stem cell sample from the patient may particularly comprises patient-derived bone marrow stem cells or hematopoietic stem cells.

In yet another aspect, an αHIV-Grp1 intron construct is provided. In some embodiments, the construct may be defined as comprising a 3' apoptosis-inducing gene sequence; (b) an external guide sequence (EGS); (c) an internal guide sequence (IGS); and (d) a conserved HIV targeting sequence that corresponds to an HIV genome Primer Binding Site (PBS), a Primer Activation Site (PAS), or a combination thereof. In some embodiments, the αHIV-Grp1 intron construct may be defined as a PAS126 intron, a PAS128 intron, a PBS 182 intron, or a LOOP 126 intron.

BRIEF DESCRIPTION OF THE DRAWINGS

FIG. 1a—Group I intron structure and activity. Left: Structural features of Trans-splicing Group I introns showing alignment with the target sequence (top strand, left (5') to right (3'), SEQ ID NO: 1), the relative positions of the antisense IGS and EGS (bottom strand, right (5') to left (3') SEQ ID NO: 2), as well as the P10 helix (embedded as "UCCUCG", left (5') to right (3') within SEQ ID NO: 3), and intron catalytic core (Intron) (sequence not shown). FIG. 1b: Trans-splicing reaction catalyzed by the group I intron. First step: Intron finds its target RNA sequence through complimentary base pairing with the guide sequences. The 3' GNP OH attacks the phosphodiester backbone directly downstream of the reactive uracil on the 5' exon. Second step: The 3' exon is brought into proximity with the newly freed 3'-OH on the cleavage uracil, guided by the P10 helix. The 3'-OH attacks the phosphodiester backbone just upstream of the 3' exon in another transesterification reaction, resulting in the 5' exon and the 3' exon being joined covalently. The end result is a new RNA molecule.

FIG. 6: Sequencing results of RTPCR recovered splice products from in vitro trans-splicing reactions with PBS-PAS targeting Group I introns. Sequence alignments are shown for different introns with the splice junctions located between the indicated nucleotides (noted between V characters above the coordinate positions) and differences between experimental and expected results noted by a * below the appropriate nucleotides in the bottom row of expected results. The ATG start codon of the 3' exon encoding a polypeptide capable of inducing apoptosis in a cell, exemplified by ATG GTC ATA G. (corresponding to nucleotides 24-32 of SEQ ID NO: 8), is underlined in the bottom row of expected results for the PAS126 Sequence Alignment, and corresponding codon sequences in the PAS128, PBS182, and LOOP128 Sequence Alignments.

DETAILED DESCRIPTION OF THE EMBODIMENTS

Figure 1A:
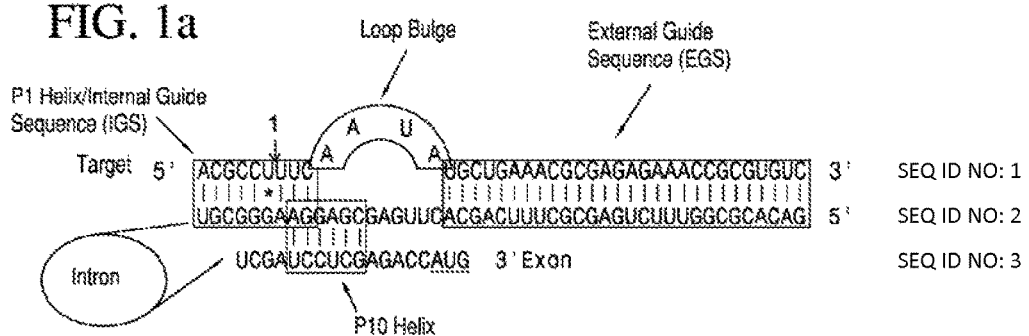
FIG. 1a-1b.

Presented are αHIV-Grp1 intron constructs that are useful in the control and inhibition of HIV infection. Methods employing these constructs are also provided that present a method for treating and/or curing HIV and the progression thereof the AIDS. Several assays for trans-splicing activity are provided that employ both artificial sequences and infectious targets. These designs involve the addition of an extended external guide sequences (EGS) that functions to improve recognition, alteration of a p10 helix to provide an even more favorable splicing context, and lesser conserved targets within the same region of the HIV genome. A quantitative RT-PCR protocol is developed to make more quantitative comparisons of the data.

Example 1—Construction of Retroviral Vectors

The present example demonstrates the construction and use of retroviral vectors containing αHIV-Grp1 introns having a 3' apoptosis-inducing gene to establish transformed cells that constitutively express these selected Group I introns, and that may be used in the treatment and cure of a human immunodeficiency virus in an animal. These transformed cells are challenged with active HIV virus to demonstrate the efficacy of the introns in suppressing lentivirus infections in the transformed cell cultures. Retrovirus vectors will be constructed for transduction of these expressed introns in HEK293 cells.

Following selection and cell sorting, the effectiveness of these introns in suppressing HIV infection of these transformed cell cultures will be assessed.

Example 2—Apoptosis-Inducing Gene Products for Suppression of HIV Infection

The present example demonstrates the effectiveness of alternative apoptosis-inducing gene products for suppression of HIV infection in the present αHIV-Grp1 intron strategy. Initial examinations into apoptosis inducing gene products focused on the tBax inducer. While the tBax protein has proven to be an effective inducer of apoptosis in both the mosquito cell and human cell applications, it does not have enzymatic activity, and may therefore be inferior to other inducers of apoptosis such as Caspases. The present invention will employ certain caspases as an alternative 3' exon for apoptotic induction following trans-splicing.

Example 3—Hematopoietic Stem Cell Replacement

The present example presents a transgenic αHIV-Grp1 intron hematopoietic stem cell replacement strategy in a mouse system. A chimeric HIV virus will be used that has an the envelope coding domain from an ecotropic MLV that restricts replication of the chimeric virus to rodents (Potash et al., 2005). This will be used to establish infections in young adult mice. These mice will serve as models for the present transduced hematopoietic stem cell therapies using the αHIV-Grp1 introns.

While this proposal is designed to validate this approach using a less costly and more rapid mouse system, the data provided will serve to provide support for the successful expectation of the use of this approach in simian models.

This invention provides a means of eradicating HIV virus from an infected individual. This strategy will be effective either alone or in conjunction with other strategies currently being used and/or proposed for use for transduced hematopoietic stem cell therapies.

Example 4—Studies Targeting Conserved Sequences of the HIV Genome

Figure 5:
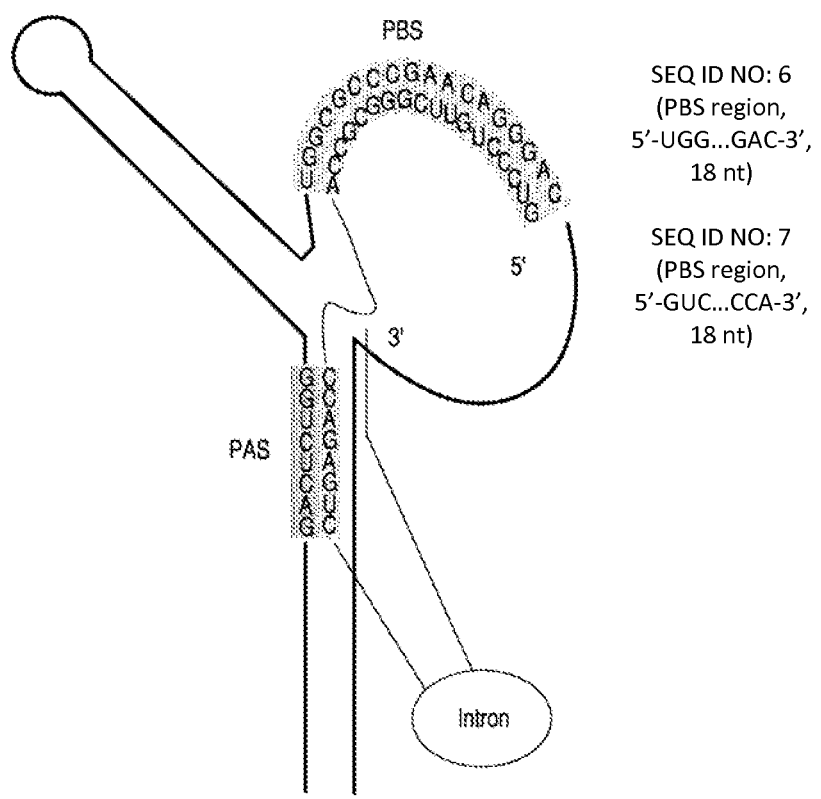
FIG. 5: Schematic depicting the binding of the Loop126 anti-HIV group I introns to the conserved PBS (SEQ ID NO: 6) and its complement (SEQ ID NO: 7) and PAS sequences. The intron binds in a similar way as the $tRNA^{lys3}$ binds to these sequences, allowing a large loop bulge which forms a natural stem loop structure. Such a large loop bulge region has previously never been designed into a trans-splicing Group I intron, and is one of the innovative aspects of the design of these introns. The fact that incorporation of such a large loop bulge does not significantly detract from the trans-splicing activity permits applications of these introns where conserved regions are separated by more than a few non-conserved sequences.

Two sequences that are highly conserved within the HIV genome are the ψ-packaging signal (Amarasinghe et al., 2000) near the 5' end of the gag gene and the adjacent upstream tRNA$^{lys3}$ primer binding site (PBS). The accessibility of these conserved sequences to Group I intron attack was examined by constructing a 540 nt long target sequence encompassing the 5' terminus of the HIV genome and including the tRNA PBS and ψ-packaging signal (FIG. 5).

Group I introns targeting the ψ-packaging signal were unsuccessful because the targeted sequence for cleavage occurred in a complex of stem loop structure that was not accessible to the intron under normal physiological conditions.

The tRNA$^{lys}$ primer binding sequence was then examined. The tRNA$^{lys}$ primer binds the host genome at three sites: the PBS (Primer Binding Site), the PAS (Primer Activation Signal), and anticodon recognition sequence (Dobard et al., 2007). Abbink et al., (2004) recognized that the PBS is almost completely conserved across HIV as it is encoded by the tRNA primer[19]. The PBS-tRNA interaction is stronger than the other two sites because of the greater number of base pairs. A point mutation in the PBS has been seen to occur if a virus uses tRNA$^{lys5}$ to prime reverse transcription instead, but frequently this mutation will revert by binding tRNA$^{lys3}$ imperfectly in the next generation's reverse transcription. The PAS motif also appears to be necessary to initiate reverse transcription and thus should also be well conserved.

A Quick Align search using the Los Alamos National Laboratory HIV sequence database reveals the PAS is fairly well conserved, though a few point mutations exist within several viral clades. The PBS is nearly perfectly conserved across the major clades B, C, and D. Clades B is the most prominent clade in the US and Western Europe, and displays a highly conserved PBS and PAS, while Clade D, prevalent in Eastern Europe and Sub-Saharan Africa, display 100% conserved PBS and PAS. In nearly all sequences the PBS's upstream flanking sequence is perfectly conserved as well. Unfortunately, the first several hundred nucleotides of the viral genome (including the presently described sequence of interest) are not well represented in Los Alamos' sequence database, and the smaller number of sequences observed could misrepresent the true conservation of the PAS and PBS. By both the conservation and accessibility, it was determined that the PAS and PBS would be good candidates for intron targeting.

Example 5—Design and Testing of αHIV-Grp1 Introns

Targetable uracils were identified, two within the PAS (U126 and U 128) and one within the PBS (U182). Four introns were then designed. Three standard introns targeted each uracil (PAS 126, PAS 128, PBS 182), and a fourth (LOOP 126) targets U 126 from the PAS and base pairs with the PBS via EGS. This latter intron is quite different from the previously designated introns, and novel among all published introns, as the region of non-homology termed the "loop bulge" in the target HIV RNA is a rather large stem loop that forms between the PAS and PBS sequences (FIG. 5, and SEQ ID NOS: 6 and 7). The intron models tRNA$^{lys3}$ in binding both PAS and PBS. Successful splicing was observed in our in vitro reaction system for each of the Group I introns targeting the PBS and PAS sequences (FIG. 6).

Figure 7A:
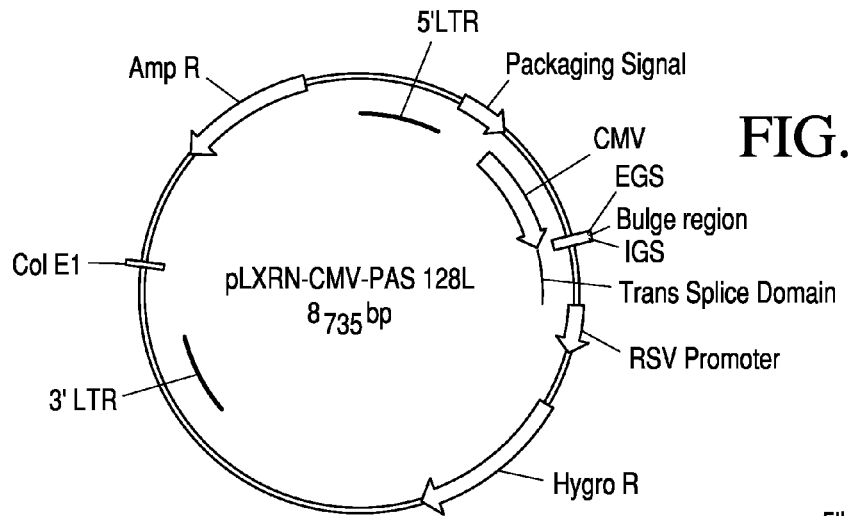
FIG. 7: Trans-splicing activity of αHIV-Grp1 introns in transiently co-transfected 293 cells. A. Lentivirus expression plasmids were constructed to express the αHIV-Grp1 introns from the CMV promoter. B. The target transcript for firefly luciferase was expressed from the native HIV-1 LTR promoter to generate transcripts having the 5' terminal sequences of native HIV, including the PBS and PAS targets. C. Target transcript, αHIV-Grp1 introns, and splice products were detected in cells 96 hours post transfection using RT-PCR with sequence specific primers. The introns PAS 128 and PAS 128L (L stands for long external guide sequence) yielded the best results in this assay.
Figure 7B:
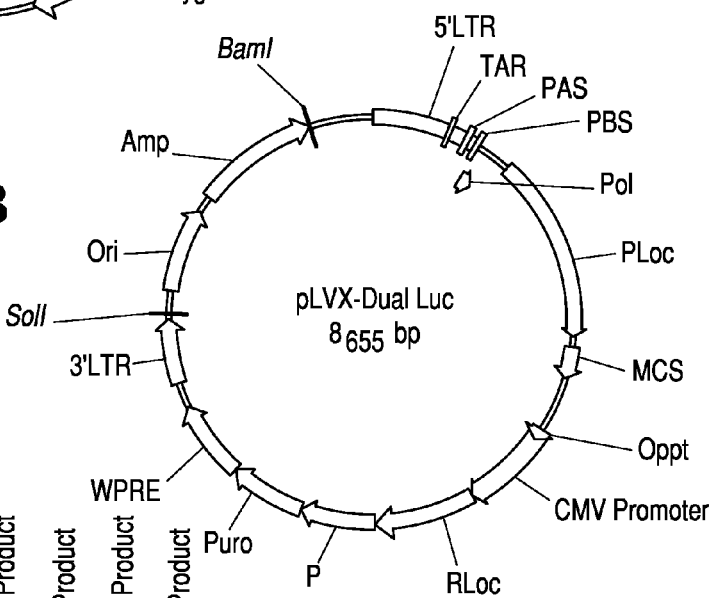
Figure 7C:
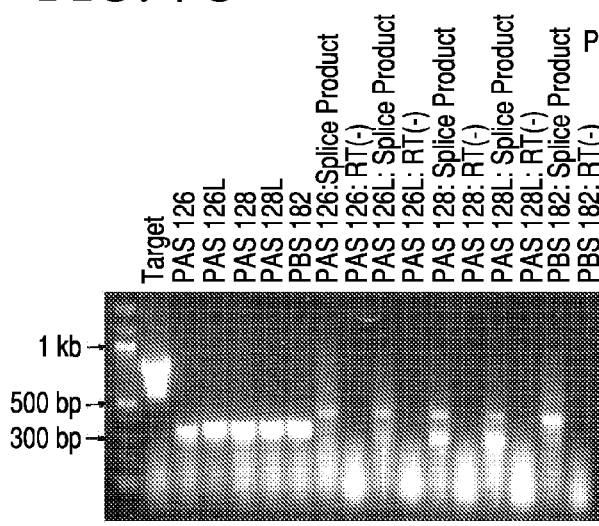

Splicing assays were also performed against target plasmids containing the 5' LTR sequence of HIV-1 in transiently transfected 293 cells. Each αHIV-Grp1 intron was expressed from the CMV promoter of a lentiviral vector construct (FIG. 7b) in the presence of a co-transfected plasmid that expressed a firefly luciferase gene transcript from the HIV-1 LTR (see FIG. 7b). The resulting RT-PCR analysis (FIG. 7c) revealed the presence of spliced product, and subsequent analyses confirmed proper splicing of the 3' exon by the αHIV-Grp1 introns.

Example 6—Confirmation of αHIV-Grp1 Intron Activity Against HIV

While activity assays against the plasmid-encoded LTR-linked sequences demonstrated the splicing activity of the αHIV-Grp1 introns, the present study was conducted to confirm that this activity would translate into an effective suppression of HIV in a productively infected cell.

A preliminary study was conducted using the αHIV-Grp1 intron 128L. A previously developed GFP labeled HIV virus clone, HIV iGFP (Hubner et al., 2007), was employed. This clone that allows fluorescent quantification of virus production in 293 cells. Virus produced with this clone was used to establish infection in 293 cells for 48 hours, at which time the infected cells were transfected with pLXRN CMV vectors (see FIG. 7A) expressing αHIV-Grp1 introns having either nonsense sequence or tBax as the 3' exon. After a further 96 hours, virus was collected from the supernatants and the EGFP fluorescence was quantified using a Spectramax M5e.

Figure 8:
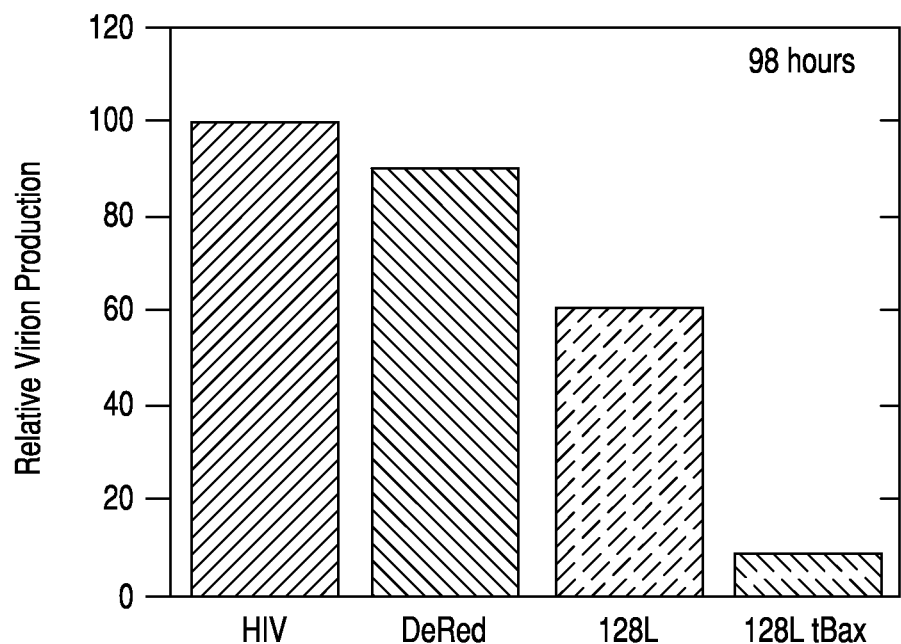
FIG. 8: Cells were infected with the HIV-iGFP chimeric fluorescent virus, incubated for 48 hours, and then transfected with pLXRN CMV expression vectors expressing αHIV-Grp1 intron 128L either with (128L tBax) or without (128L) an attached 3' tBax exon. Controls were HIV-iGFP infection alone (HIV) and post infection transfection with a DsRed expression plasmid (DsRed). Virus amounts are recorded as relative fluorescence in virus supernatants, and are relative to the HIV infection control.

The results (FIG. 8) clearly show a significant reduction in the production of labeled virus in the presence of the αHIV-Grp1 intron, whether or not tBax was used as the 3' exon. In the absence of tBax, reduction levels reflect the inhibition of new virus as a result of the activity of the ribozyme alone. In contrast, when tBax is substituted as the 3' exon, virus reduction is even greater.

Because these assays were done using transfected expression plasmids and established HIV infections in the cells, they may not accurately reflect the levels of reduction expected if cells are first transformed to express the αHIV-Grp1 intron and then challenged with HIV. In fact, priming the cells with expressed αHIV-Grp1 intron prior to infection with virus should lead to significantly better protection of the cultures and significantly greater reductions of produced virus.

Example 7—HIV Treatment and Validation

The present example validates an αHIV-Grp1-apoptosis effector molecule for suppression of HIV in transgenic hematopoietic stem cell replacement therapies. The method is designed to ultimately test the efficacy of this approach in an animal model system. The model system of choice for these first analyses is the mouse. This strategy as validated in this less expensive, more easily analyzed model system will provide a solid foundation to propose later primate studies.

The present example presents the construction and evaluation of additional αHIV-Grp1 introns utilizing the several previously established assays for trans-splicing activity employing both artificial sequences and infectious virus targets.

While the present initial results with constructing and testing αHIV-Grp1 introns have been relatively productive in that one intron has been identified that seems to have optimal activity, improvements in the activity of the other introns designed can be made with further design changes. These design changes involve the addition of extended external guide sequences (EGS), alterations of the p10 helix to provide a more favorable splicing context, and examination of less conserved targets within the same region of the genome. The present intron constructs also include an Internal Guide Sequence (IGS), whose sequence/structure may also be optimized for the present intron constructs.

Bell et al. (2004) suggest several ways to optimize the activity of Group I introns. For example, shortening the P10 helix and lengthening the P9.0 domain to eight base pairs can increase the efficiency of the second step reaction of trans-splicing.

Study Design:

An in vitro, transiently transfected cell system will be used, and HIV-iGFP assays will be utilized for determining the activity of each αHIV-Grp1 intron. All assays will employ RT-PCR as a first analysis to confirm splicing activity. A quantitative RT-PCR protocol will be developed to make more quantitative comparisons of the data. Up until this point the data have been qualitative only with respect to the RT-PCR analyses, and even though there may appear to be differences in activities in the in vitro and transient transfection assays, these differences may reflect subtle differences in assay conditions or variability in concentrations of substrate and intron rather than true differences in activity of the introns.

Activities of all new constructs will be evaluated against the 128L standard as a control. While consistently good results were obtained with the 128L intron in the present assays, other introns may also be similarly effective if the assays are repeated and optimized. In addition, while this standard may represent the most effective intron under conditions of the assays, further examination of the introns may be pursued that appear to yield somewhat less effective results in the context of these particular assays in the event that acceptable results would still be obtained when applied in the context of the transformed cell assays as described in above.

Retroviral vectors containing αHIV-Grp1 introns having 3' apoptosis-inducing genes will be constructed and used to establish transformed cells that constitutively express these selected Groups I introns. These transformed cells will be challenged with active HIV virus to test the efficacy of the present introns in suppressing lentivirus infections in transformed cell cultures.

Thus far none of the assays employed to test the activity of the present αHIV-Grp1 introns are reflective of the actual conditions under which the introns are expected to be employed in an HIV infection suppression scenario. For this reason, transformed cell cultures will be developed that constitutively express the αHIV-Grp1 intron, and will then be exposed to low levels of infectious HIV virus.

Transformed 293 cells will be prepared that express the present αHIV-Grp1 introns. Cultures of these transformed cells will then be used to determine the effectiveness of these introns in suppressing HIV infection. To do this, the retrovirus vectors will first be altered for transduction of the expressed introns in a way that permits optimized selection of the resulting transformed cells.

(a). Modification of the pLXRN-Based Vector to Express the mCherry Fluorescent Marker Gene:

The pLXRN-CMV base vector will be altered to incorporate an ECMV IRES directed mCherry downstream of the 3' exon of the αHIV-Grp1 introns. The effectiveness of incorporating an IRES expressed downstream introns has already been demonstrated (Carter et al., 2010). The advantage of employing this intimately linked marker gene is two-fold. First, this will establish that if cells are expressing the mCherry, they are also expressing the αHIV-Grp1 intron, since both are part of the same di-cistronic transcript. Second, the mCherry fluorescence provides a handle useful to sort the transformed cells for enrichment following hygromycin selection.

In previous analyses with the αDENV-Grp1 introns, a level of background DEN virus infection was observed in hygromycin selected cultures. This level may be due to the presence of hygromycin resistant untransformed cells in the cultures because these levels are influenced by the stringency of selection and the freshness of the hygromycin. To insure optimal results, inclusion of a marker that can provide a handle for cell sorting may be used.

Finally, by validating this IRES-coupled gene expression approach with respect to the αHIV-Grp1 introns, the introduction of a coupled selectable gene that may be useful in subsequent development of in vivo applications is supported. Specifically, this will establish that it is possible to provide an IRES-expressed, intimately linked gene that under given conditions (e.g., drug exposure), would permit selective amplification of transformed hematopoietic stem cells in a patient without the need for the more extreme measure of first ablating the immune system.

(b.) Transformation of 293 Cells with Lentivirus Vectors Expressing the αHIV-Grp1 Introns and Testing for HIV Infection.

293 cells will be infected with each lentivirus vectors at an MOI of 10 to insure relatively complete infection of the cell culture. Following a 72 hour recovery period, the cells will be subject to staged selection with hygromycin over a three week period, monitoring mCherry fluorescence to insure enrichment for those cells expressing the αHIV-Grp1 intron. The expression of each intron will also be confirmed using qRT-PCR. Following the three week selection period we will sort the cell populations using a BD Biosciences FACSAria III cell sorter to enrich for optimal expression of the mCherry marker, which should also insure optimal expression of the αHIV-Grp1 intron.

The negative control for trans-splicing activity will be produced by removing of domains P4 through P6 of the trans-splicing domain (Cech, 1990). Domains P4 to P6 must be removed instead of only the Pabc5 domain, as previously described (Ayre et al. 1999), since in our previous analyses αDENV-Grp1 ΔPabc5 retained residual activity. Domains P4, P6 and Pabc5 form an extensive interface with each other to form the basis of the catalytic core (Murphy and Cech 1993; Murphy and Cech 1994; Cate et al. 1996).

(c.) Challenge of αHIV-Grp1 Intron Expressing Cells with HIV:

The HIV-iGFP virus (Hubner et al., 2007) will be used as well as wild type NL4-3 in assays for the effectiveness of HIV suppression in our transformed cell cultures. While the HIV-iGFP mutant virus has the advantages of ease of assaying, there are some problems with relative infectivity compared with the wild type virus (Muller et al., 2004). In addition, the fluorescent counts alone cannot be considered reliable predictors of actual infectious virus production. Therefore, the standardized p24 assays will be used as well as qRT-PCR assays to determine the relative effectiveness of our αHIV-Grp1 introns in suppression of virus infection of the transformed cells. Finally, the effectiveness of the apoptotic response will be assessed using Annexin V staining to confirm that apoptotic cell death is occurring in HIV-challenged cultures.

iii.) Examining the Relative Effectiveness of Alternative Apoptosis-Inducing Gene Products for Suppression of HIV Infection in our αHIV-Grp1 Intron Strategy.

While the tBax protein has proven to be an effective inducer of apoptosis in both the mosquito cell and human cell applications, it does not have enzymatic activity that could effectively enhance its performance. The buildup of sufficient tBax is relied upon as a result of the splicing and translation reaction, and as a result this may not be the a somewhat less effective means of inducing apoptosis than generating a protein with enzymatic properties.

It may be more advantageous to use caspases as a 3' exon since it takes multiple tBax molecules to form a single pore, while the enzymatic activity of the caspase amplified its effect within the cell. Listed below are several caspases that may be of interest.

Caspase 3:

Activated in the apoptotic cell both by extrinsic (death ligand) and intrinsic (mitochondrial) pathways making this the most logical candidate as the expression of the active form of this caspase would activate both pathways simultaneously (Salvesen 2002; Ghavami et al., 2009), leading to activation of other caspases that will cleave of cellular substrates and resulting in apoptosis.

Caspase-6:

Plays a central role in the execution phase of apoptosis activating targets following activation by initiator caspases (Cowling and Downward, 2002). Activation of caspase 6 in the absence of initiator caspases in cells would lead to the initiation of apoptosis without down regulation of this event by inhibitors of apoptosis (IAP) that act upon initiator caspases.

Caspase 8:

An initiator caspase. According to the "induced-proximity model" (Salvensen and Dixit, 1999) procaspase-8 undergoes autoproteolytic cleavage, following recruitment to the death-inducing signaling complex (DISC) forming active caspase-8, which in turn can activate other procaspases, leading to cleavage of cellular substrates, and apoptosis.

Caspase-9:

Activated Caspase-9 is able to cleave Caspase-3 (Li et al., 1997) leading to initiation of the extrinsic and intrinsic apoptotic pathways.

Each of these caspases exists in an inactive and an active form. In some cases modification of the sequence can lead to a constitutively active enzyme that, when expressed, will irreversibly induce apoptosis (Srinivasula et al., 1998). These sequences may be designed to serve as 3' exons similarly to the way we designed the tBax 3' exon.

Sequences encoding the active forms of each caspase will be placed in the 3' exon position of the 128L αHIV-Grp1 intron for comparative analysis of their effectiveness in inducing apoptotic cell death in transformed 293 cells challenged with HIV. The standard assays for splicing and apoptosis induction will be performed as above.

iv.) Modeling a Transgenic αHIV-Grp1 Intron Hematopoietic Stem Cell Replacement Strategy in a Mouse System.

Mouse models for HIV infection are limited in their relevance, particularly when considering immunological responses. Even humanized mouse models fall short of predictive validity in this respect. However, the approach here examined does not rely on immune function for its effectiveness. In fact, immune function is irrelevant to the characterization of the effectiveness of the present αHIV-Grp1 intron as a suppressive tool. Therefore, an appropriate mouse model could provide a cost effective and rapid means for obtaining valuable information justifying this transgenic hematopoietic stem cell replacement strategy.

Instead of relying on the more complex humanized mouse models, a chimeric HIV virus, Eco-HIV will be utilized that is built upon the clade B NL4-3 backbone. This virus has a replacement of the HIV gp120 sequence with the envelope coding domain from an ecotropic MLV that restricts replication of the chimeric virus to rodents (Potash et al., 2005). Infection of mice with this virus produces the repertoire of infected cell types typical of an HIV infection. Any mouse strain of choice may be inoculated with this chimeric virus and results in infection of all major target cell types of HIV-1. Virus burdens in the spleen are comparable to HIV-1 burdens in resting lymphocytes in human (Potash et al., 2005). Therefore, this chimeric virus in the mouse system seems to be good choice for the present studies.

The chimeric virus will be used to establish infections in young adult (8-10 weeks) mice for a six week period. To insure complete infection we will sample hematopoietic tissues, particularly lymphocyte and macrophage populations, for the Eco-HIV virus. Assays will include circulating virus assays as well as PCR assays of provirus. Once infection has been established mice will be irradiated and/or subjected to chemical myeloablation followed by transfusion through tail vein with αHIV-Grp1 intron transformed syngeneic hematopoietic stem cells. The HIV infection will be held in check with drug therapies to allow reconstitution of the immune system within the mice in the absence of significant virus load. Lymphocyte and macrophage cell populations will be monitored to insure full reconstitution. This strategy models clinical protocols for hematopoietic stem cell therapies (e.g. Cartier et al., 2009). Following the reconstitution of the immune system the antiviral therapy will be removed and the levels of lymphocyte and macrophage cell populations will be monitored to determine the impact of the active infection on these transformed cells. It is expected that there will be a reduction in the cell counts for HIV susceptible cell populations as a result of the impact of the DUI activity. The virus and provirus load will also be monitored to establish maintenance of a low viremia.

A unique and revolutionary strategy for combating and curing HIV infections is provided with the present anti-HIV Group 1 intron strategies. By providing reconstituted susceptible cells with a targeted trans-splicing molecule that generates apoptotic cell death in the presence of the HIV mRNA substrate following infection, the ability of the virus to re-establish infection in the transduced reconstituted immune cells is eliminated. This has the dual effect of stabilizing the viral load at sub-clinical levels, as well as acting as a "sponge" for virus shed from long term reservoirs. The key to this approach is successful attack of invariant sequence within the HIV genome, which have been identified and confirmed are subject to trans-splicing. Another advantage of this approach is the ability to couple the trans-splicing intron to an IRES-expressed gene product with allows for engineering of a selective genes that insures maintenance of the transgene in reconstituted tissues, and may also allow repopulation of the immune system without myeloablation therapies.

BIBLIOGRAPHY

The following articles are specifically incorporated herein by reference in their entirety.

Abink Truus E, et al. 2004. "Forced Selection of a Human Immunodeficiency Virus Type 1 Variant That uses a Non-Self tRNA Primer for Reverse Transcription: Involvement of Viral RNA Sequences and the Reverse Transcriptase Enzyme". *J. Virol.* 78(19), 10706-10714. PMID:15367637

Allers K, Hütter G, Hofmann J, Loddenkemper C, Rieger K, Thiel E, and Schneider T, 2010. "Evidence for the cure of HIV infection by CCR5{Delta}32{Delta} stem cell transplantation". *Blood Journal*, doi: 10.1182/blood-2010-09-309591.

Ayre B G, Kohler U, Good H M, and Haselhoff J. 1999. "Design of Highly specific cytotoxins by using trans-splicing ribozymes". *Proceedings of Nat. Acad. Of Science.* 96(7):3507-12. Mar. 30, 1999. PMID:10097066

Bell M, Sinha J, Johnson A, and Testa S. 2004. "Enhancing the Second Step of the Trans Excision-Splicing Reaction of a Group I Ribozyme by Exploiting P9.0 and P10 for Intermolecular Recognition". *Biochemistry* 43:4323-4331. Mar. 16, 2004. PMID:15065876.

Blankson Joel N, et al. 2002. "The Challenge of Viral Reservoirs in HIV-1 Infection: *Annu. Rev. Med.* 53, 557-593. PMID:11818490.

Byun J, Lan N, Long M, Sullenger B A, 2003. "Efficient and specific repair of side beta-globin RNA by trans-splicing ribozymes". Rna 9:1254-1263. PMID:13130139.

Carter J, Keith J H, Barde P V, Fraser T, Fraser M J, 2010. "Targeting of Highly Conserved Dengue Virus Sequences with anti-Dengue Virus Trans-splicing Group I Introns". BMC Molecular Biology, 2010 11:84 Nov. 15, 2010. PMID:21078188—in progress.

Cartier N, et. Al. 2009. "Hematopietic stem cell gene therapy with a lentiviral vector in x-linked adrenoleukodystrophy". Science. Vol 326. Nov. 6, 2009. PMID: 19892975

Cate J H, Gooding A R, Podell E, Zhou K, Golden B L, Kundrot C E, Cech T R, and Doudna J A. 1996. "Crystal structure of a Group I ribozyme domain: principles or RNA packing". *Science.* 273:(5282:1678-85. Sep. 20, 1996. PMID:8781224.

Cech T R. 1990. "Self-splicing of Group I Introns: *Annual Review of biochemistry.* 59:543-568. PMID:2197983.

Cowling V, and Downward J. 2002. "Caspase-6 is the direct activator of caspase-8 in the cytochrome c-induced apoptosis pathway: absolute requirement for removal of caspase-6 prodomain". *Cell Death and Differentiation.* 9:1046-1056. PMID:12232792.

Dobard Charles W, et al. 2007. "Molecular Mechanisms by Which Human Immunodeficiency Virus Type 1 Integrase Stimulates the Early Steps of Reverse Transcription". J. Virol., 81(18), 10037-10046.

Freund F, Boulm F, Michel J, Ventura M, Moreau S, and Litvak S. 2001 "Inhibition of HIV-1 replication in vitro and in human infected cells by modified antisense oligonucleotides targeting the tRNALys3/RNA initiation complex" *Antisense Nucleic Acid Drug Dev.* 11(5):301-15. October 2001. PMID:11763347.

Ghavami S, Hashemi M, Ande S R, et. Al. 2009. "Apoptosis and cancer: mutations within caspase genes". *J. Med. Genet.* 46:497-51-. Jun. 7, 2009. PMID:19525876.

Hüibner W, Chen P, Portillo A, Liu Y, Gordon R, and Chen B, 2007. "Sequence of Human Immunodeficiency Virus Type 1 (HIV-1) Gag Localization and Obligomerization Monitored with Live Confocal Imaging of a Replication-Competent, Fluorescently Tagged HIV-1". *Journal of Virology.* Doi10.1128/JVI.01088-07, 12596-12607. November 2007. PMID:17728233.

Jung H S, Kwon B S, Lee S W, 2005. "Tumor-specific gene delivery using RNA-targeting Tetrahymena group I Intron". Biotechnol Lett 27:567-574. PMID:15973491.

Jung H S, Lee S W, 2006. "Ribozyme-mediated selective killing of cancer cells expressing carcinoembryonic antigen RNA by targeted trans-splicing". *Biochem Biophys Res Commun* 349:556-563. PMID:16945335.

Kastanos E, Hjiantoniou E, Phylactou L A, 2004. "Restoration of protein synthesis in pancreatic cancer cells by trans-splicing ribozymes". Biochem Biophys Res Commun 322:930-934. PMID:15336553.

Kim A, BanG, Song M S, Bae C D, Park J, Lee S W, 2007. "Selective regression of cells expressing mouse cytoskeleton-associated protein 2 transcript by trans-splicing ribozyme". Oligonucleotides 17:95-103. PMID: 17461766.

Kohler U, Ayre B G, Goodman H M, Haseloff J, 1999. "Trans-splicing ribozymes for targeted gene deliver". *J Mol Biol* 285:1935-1950. PMID9925776.

Kruger K, Grabowski P J, Zaug A J, Sands J, Gottschling D E, Cech T R, 1982. "Self-splicing RNA: autoexcision and autocyclization of the ribosomal RNA intervening sequence of Tetrahymena". Cell 31:147-157. PMID: 6297745.

Kwon B S, Jung H S, Song M S, Cho K S, KIM S C, Kimm K, Jeong J S, Kim I H, Lee S W, 2005. "Specific regression of human cancer cells by ribozyme-mediated targeted replacement of tumor-specific transcript". *Mol Ther* 12:824-834. PMID:16040278.

Lamothe B, and Joshi S, 2000. "Current Developments and Future Prospects for HIV Gene Therapy Using Interfering RNA-Based Strategies". Front. Biosci., 5, 527-555. PMID10799355

Lander E S, et al., 2001. "Initial sequencing and analysis of the human genome". *Nature* 409:860-921. PMID: 11237011

Li P, Nijhawan D, et. Al. 1997. "Cytochrome c and dATP-dependent formation of Apaf-1/Caspase-9 complex initiates an apoptotic protease cascade". *Cell* 91:479-489. Nov. 14, 1997. PMID:9390557.

Müller B, Daecke J, Fackler O, Dittmar M, Zentgraf H, and Kräusslich H-G. 2004. "Construction and Characterization of a Fluorescently Labeled Infectious Human Immunodeficiency Virus Type 1 Derivative". Journal of Virology, 10.1128/JVI.78.19.10803-10813.2004 p. 10803-10813. October 2004. PMID:15367647.

Murphy F L, and Cech T R. 1993. "An independently folding domain of RNA tertiary structure within the Tetrahymena ribozyme". Biochemistry. 32:5291-53—. May 1993. PMID:7684607.

Murphy F L, and Cech T R, 1994. "GAAA tetraloop and conserved bulge stabilize tertiary structure of a Group I intron domain". Jour. Of Molecular Biology. 11:236, 49-63. February 1994. PMID:8107125.

Nawtaison P, Keith J, Fraser T, Balaraman V, Kolokoltsov A, Davey R A, Higgs S, Mohammed A, Rongsriyam Y, Komalamisra N, Fraser M J, 2009. "Effective Suppression of Dengue Fever Virus in Mosquito Cell Cultures using retroviral transduction of Hammerhead Ribozymes Targeting the Viral Genome". *Virology Journal,* 2009 6:73 (Jun. 4, 2009). PMID: 19497123.

Potash M J, Wei C, Bentsman G, Paris N, Saini M, Nitkiewicz J, Belem P, Sharer L, Brooks A, Volsky D. 2005. "A mouse model for study of systemic HIV-1 infection, antiviral immune responses, and neuroinvasiveness". PNAS 102:10; 3760-3765. Mar. 8, 2005. PMID: 15728729.

Rossi John J, et al. 2007. "Genetic therapies against HIV". Nat. Biotechnol., 25(12), 1444-1454. December 2007. PMID:18066041.

Ryu K J, Kim J H, Lee S W, 2003. "Ribozyme-mediated selective induction of new gene activity in hepatitis C virus internal ribosome entry site-expressing cells by targeted trans-splicing". Mol Ther 7:386-395. PMID: 12668134.

Salvesen G, 2002. "Caspases: opening the boxes and interpreting the arrows". *Cell Death and Differentiation.* 9:3-5. PMID:11803369.

Salvesen G, and Dixit V. 1999. "Caspase activation: The induced-proximity model". Colloquium Paper. *Proceedings of the National Academy of Sciences.* Feb. 20-21, 1999. PMID:10500109.

Srinivasula S. Ahmad M, et. al. 1998. "Generation of Constitutively Active Recombinant caspases-3 and -6 by Rearrangement of their subunits". *Journal of Biological Chemistry.* 273:17. Apr. 24, 1998. PMID:

Sullenger B A, Cech T R, 1994 "Ribozyme-mediated repair of defective mRNA by targeted, trans-splicing" Nature 371:619-622. PMID 7935797.

Waterston R H, et al. 2002. "Initial sequencing and comparative analysis of the mouse genome". *Nature* 420:520-562. Dec. 5, 2002. PMID:12466850.

Won Y S, Lee S W, 2007. "Targeted retardation of hepatocarcinoma cells by specific of alpha-fetoprotein RNA". *J. Biotechnol* 129:614-619. Feb. 14, 2005. PMID:1736006.

TABLE 1

List of Sequences

Figure 4:
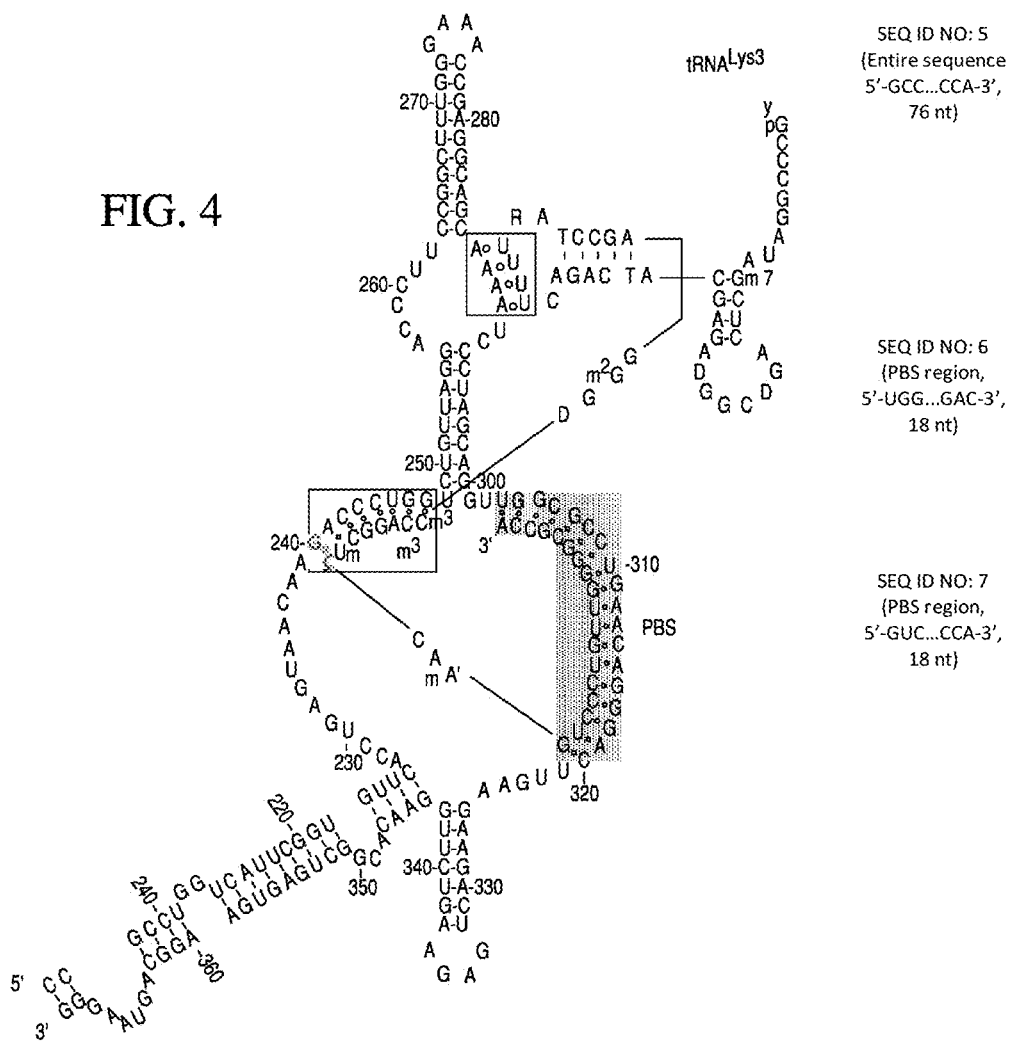
FIG. 4: $tRNA^{lys3}$ binds HIV-2 to prime reverse transcription. Binding interaction is highly conserved between HIV-1 and -2. In HIV-I PAS is "GACUCUGG" rather than HIV-2's "GACCCUGG" pictured. Initial bases added are those immediately upstream of the PBS. Figure adapted from Freund et al. (2001).

| Short Name | Organism | Description | Support | Type | Length (aa/nt) | SEQ ID NO |
|---|---|---|---|---|---|---|
| Dengue Virus 2 Target RNA | Dengue virus type 2 | misc_feature (1)..(9)<br>Target sequence in a Dengue Virus 2 RNA complementary to Internal Guide Sequence (IGS) in an exemplary trans-splicing intron.<br>misc_feature (10)..(13)<br>Loop Bulge sequence in Dengue Virus 2 RNA located between a target sequence and a sequence complementary to an External Guide Sequence (EGS) in an exemplary trans-splicing intron.<br>misc_feature (14)..(41)<br>A sequence in Dengue Virus 2 RNA complementary to an External Guide Sequence (EGS) in an exemplary trans-splicing intron targeting a uracil residue in the target sequence.<br>acgccuuuca auaugcugaa acgcgagaga aaccgcgugu c | FIG. 1a, first line | RNA | 41 | 1 |
| EGS and IGS of exemplary trans-splicing intron | Artificial | Synthetic oligonucleotide comprising EGS and IGS of an exemplary trans-splicing intron targeting a Dengue Virus 2 RNA.<br>misc_feature (1)..(28)<br>External Guide Sequence (EGS), which can be of variable length, in a trans-splicing intron targeting a viral RNA, exemplified by a Dengue virus 2 sequence, wherein the EGS is capable of forming a transient helix downstream from the target sequence.<br>misc_feature (32)..(41)<br>Internal Guide Sequence (IGS), at least 9 nt in length, targeting a viral RNA, exemplified by a Dengue virus 2 sequence, wherein the IGS is capable of forming a P1 helix with target sequence comprising one or more uracil residues.<br>gacacgcggu uucugagcgc uuucagcacu ugagcgagga agggcgu | FIG 1a, second line | RNA | 47 | 2 |
| P10 Helix 3' exon region of an exemplary trans-splicing intron | Artificial | Synthetic oligonucleotide comprising P10 Helix and AUG codon of a 3' exon of an exemplary trans-splicing intron targeting a Dengue Virus 2 RNA.<br>misc_feature (5)..(10)<br>Region in an exemplary trans-splicing intron targeting a Dengue Virus 2 RNA is complementary to a portion of the Internal Guide Sequence (IGS) of the intron capable of forming a P10 helix.<br>misc_feature (16)..(18)<br>AUG start codon in an exemplary trans-splicing intron targeting a Dengue Virus 2 RNA.<br>ucgauccucg agaccaug | FIG 1a, third line | RNA | 18 | 3 |
| HIV | HIV | misc_feature (1)..(166)<br>Residues of an HIV RNA illustrated in FIG. 4, corresponding to residues 206 to 371.<br>ccgccugguc auucgguguu caccugagua acaagacccu ggccuguuag gacccuucuu 60<br>gcuuugggaa accgaggcag gaaaaucccu agcagguugg cgcccgaaca gggacuugaa 120<br>gaagacugag aagucuugga acacggcuga gugaaggcag uaaggg 166 | FIG. 4 | RNA | 166 | 4 |
| tRNA-Lys3 | Human tRNA-Lys3 | tRNA (1)..(76)<br>Sequence corresponding to tRNA-Lys3 complementary to a portion of the 5 end of an HIV RNA, including an HIV Primer Activating Sequence (HIVPAS) and an HIV Primer Binding Sequence (HIVPBS).<br>gcccgauag cucagdcggd agagcaucag acuuuurauc ugagggdcca gggurcaagu 60<br>cccuguucgg gcgcca 76 | FIG. 4 | tRNA | 76 | 5 |
| HIV Primer Binding Site (HIVPBS) | HIV 2 | misc_feature (1)..(18)<br>Region corresponding to nucleotides 303-320 in FIG. 4 of an HIV RNA comprising an HIV Primer Binding Sequence (HIVPBS).<br>uggcgcccga acagggac | FIG. 4 | RNA | 18 | 6 |

TABLE 1-continued

List of Sequences

Figure 1B:
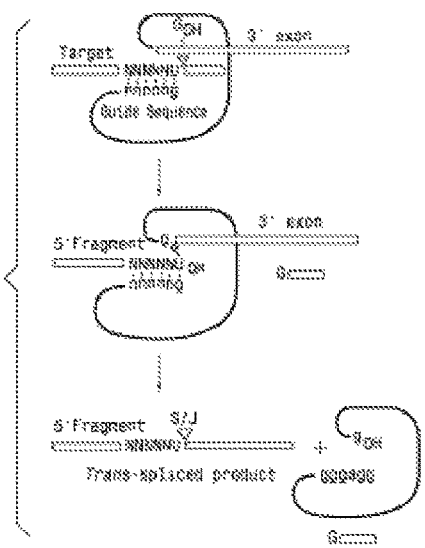
Figure 2:
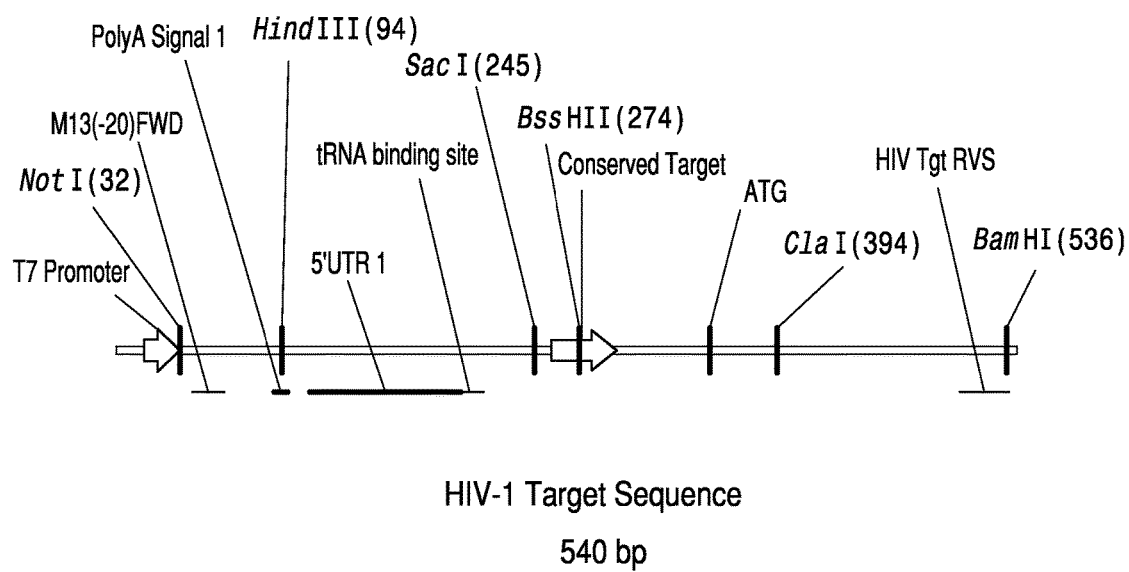
FIG. 2: The 5' region of the HIV genome was amplified from a lentivirus vector, pLVX-Puro (Clontech), inserted into the pBSK+downstream of the T7 promoter for in vitro expression as RNA.
Figure 3:
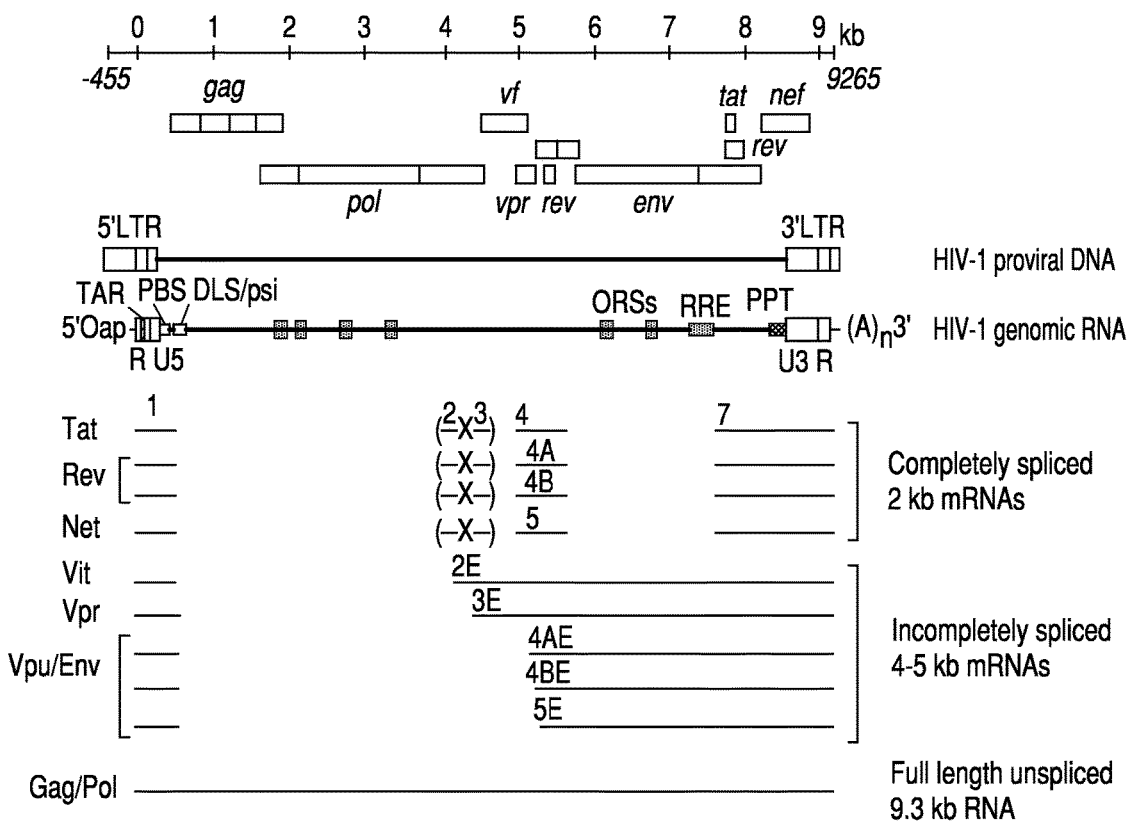
FIG. 3: Provirus sequence and transcription map showing the inclusion of the PBS at the 5' end of all transcripts produced from an integrated HIV provirus (Lamothe and Joshi (2000)).

| Short Name | Organism | Description | Support | Type | Length (aa/nt) | SEQ ID NO |
|---|---|---|---|---|---|---|
| Anti-HIVPBS in tRNA-Lys3 | Synthetic | misc_feature (1)..(18) Region in a tRNA-Lys3 complementary to the HIV Primer Binding Sequence (HIVPBS). gucccuguuc gggcgcca | FIG. 4 | RNA | 18 | 7 |
| PAS126 Splice Junction (Expected and Observed) | Synthetic | misc_feature (1)..(33) Experimental and Expected Splice Junctions for trans-splicing intron targeting U126 in HIV RNA comprising HIV sequences, intergenic region, and ATG start codon of 3' exon, illustrated in FIG. 6. ctgttgtgtg acttgcattc tgcatggtca tag | FIG. 6 | DNA | 33 | 8 |
| PAS128 Splice Junction (Expected and Observed) | Synthetic | misc_feature (1)..(34) Experimental and Expected Splice Junctions for trans-splicing intron targeting U128 in HIV RNA comprising HIV sequences, intergenic region, and ATG start codon of 3' exon, illustrated in FIG. 6. ctgttgtgtg actctggttg gaactcatgg tcat | FIG. 6 | DNA | 34 | 9 |
| PBS182W Splice Junction (Expected and Observed) | Synthetic | misc_feature (1)..(33) Experimental and Expected Splice Junctions for trans-splicing intron targeting U182 in HIV RNA comprising HIV sequences, intergenic region, and ATG start codon of 3' exon, illustrated in FIG. 6. aaatctctag cagtgtcgtg accacatggt cat | FIG. 6 | DNA | 34 | 10 |
| LOOP128 Splice Junction (Expected) | Synthetic | misc_feature (1)..(34) Expected Splice Junction for trans-splicing intron targeting U128 with an EGS targeting the HIVPBS in HIV RNA comprising HIV sequences, intergenic region, and ATG start codon of 3' exon, illustrated in FIG. 6. ctgttgtgtg actctgcttg gcattgcatg gtca | FIG. 6 | DNA | 34 | 11 |
| Loop Splice Junction (Observed) | Synthetic | misc_feature (1)..(33) Experimental Splice Junction for trans-splicing intron targeting U128 with an EGS targeting the HIVPBS in HIV RNA comprising HIV sequences, intergenic region, and ATG start codon of 3' exon, illustrated in FIG. 6. ctgttgtgtg actctgcttg ccattcatgg tca | FIG. 6 | DNA | 33 | 12 |
| HIVPAS | HIV | misc_feature (1)..(9) 9 nt target region designated HIVPAS (corresponding to nt 577 to 584 of prototype strain HIV HBX2, or nt 123 to 130 of Beerens and Berkhout) which has affinity to IGS region of trans-splicing intron gacucugg | FIGS. 4 &5 | RNA | 8 | 13 |
| HIVPBS | HIV | misc_feature (1)..(18) HIV Primer Binding Site (HIVPBS) uggcgcccga acagggac | FIGS. 4 &5 | RNA | 18 | 14 |
| IGS126 | Artificial Sequence | Synthetic Internal Guide Sequence (IGS), part of a trans-splicing intron partially complementary to and targeting uracil position U126 corresponding to nucleotide 4 in the HIVPAS sequence 5'-GACUCUGG-3' in HIV RNAs. misc_feature (1)..(9) Synthetic Internal Guide Sequence (IGS), part of a trans-splicing intron partially complementary to and targeting uracil position U126 corresponding to nucleotide 4 in the HIVPAS sequence 5'-GACUCUGG-3' in HIV RNAs. cagggucac | FIGS. 1, 7, paras [0008, 0029, 0030, 0057] | RNA | 9 | 15 |
| IGS128 | Artificial Sequence | Synthetic Internal Guide Sequence (IGS), part of a trans-splicing intron partially complementary to and targeting uracil position U128 corresponding to nucleotide 6 in the HIVPAS sequence 5'-GACUCUGG-3' in HIV RNAs. misc_feature (1)..(9) Synthetic Internal Guide Sequence (IGS), part of a trans-splicing intron partially | FIGS. 1, 7, paras [0008, 0029, 0030, 0057] | RNA | 9 | 16 |

TABLE 1-continued

List of Sequences

| Short Name | Organism | Description | Support | Type | Length (aa/nt) | SEQ ID NO |
|---|---|---|---|---|---|---|
| | | complementary to and targeting uracil position U128 corresponding to nucleotide 6 in the HIVPAS sequence 5'-GACUCUGG-3' in HIV RNAs. accggaguc | | | | |
| IGS182 | Artificial Sequence | Synthetic Internal Guide Sequence (IGS), part of a trans-splicing intron partially complementary to and targeting uracil position U182 corresponding to nucleotide 1 in the HIVPBS sequence 5'-GACUCUGG-3' in HIV RNAs. gccgcugcu | FIGS. 1, 7, paras [0008, 0029, 0030, 0057] | RNA | 9 | 17 |

```
                        SEQUENCE LISTING

<160> NUMBER OF SEQ ID NOS: 17

<210> SEQ ID NO 1
<211> LENGTH: 41
<212> TYPE: RNA
<213> ORGANISM: Dengue virus type 2
<220> FEATURE:
<221> NAME/KEY: misc_feature
<222> LOCATION: (1)..(9)
<223> OTHER INFORMATION: Target sequence in a Dengue Virus 2 RNA
      complementary to Internal Guide Sequence (IGS) in an exemplary
      trans-splicing intron.
<220> FEATURE:
<221> NAME/KEY: misc_feature
<222> LOCATION: (10)..(13)
<223> OTHER INFORMATION: Loop Bulge sequence in Dengue Virus 2 RNA
      located between a target sequence and a sequence complementary to
      an External Guide Sequence (EGS) in an exemplary trans-splicing
      intron.
<220> FEATURE:
<221> NAME/KEY: misc_feature
<222> LOCATION: (14)..(41)
<223> OTHER INFORMATION: A sequence in Dengue Virus 2 RNA complementary
      to an External Guide Sequence (EGS) in an exemplary trans-splicing
      intron targeting a uracil residue in the target sequence.

<400> SEQUENCE: 1
acgccuuuca auaugcugaa acgcgagaga aaccgcgugu c                          41

<210> SEQ ID NO 2
<211> LENGTH: 47
<212> TYPE: RNA
<213> ORGANISM: Artificial Sequence
<220> FEATURE:
<223> OTHER INFORMATION: Synthetic oligonucleotide comprising EGS and
      IGS of an exemplary trans-splicing intron targeting a Dengue Virus
      2 RNA.
<220> FEATURE:
<221> NAME/KEY: misc_feature
<222> LOCATION: (1)..(28)
<223> OTHER INFORMATION: External Guide Sequence (EGS), which can be of
      variable length, in a trans-splicing intron targeting a viral RNA,
      exemplified by a Dengue virus 2 sequence, wherein the EGS is
      capable of forming a transient helix downstream from the target
      sequence.
<220> FEATURE:
<221> NAME/KEY: misc_feature
<222> LOCATION: (32)..(41)
<223> OTHER INFORMATION: Internal Guide Sequence (IGS), at least 9 nt in
      length, targeting a viral RNA, exemplified by a Dengue virus 2
      sequence, wherein the IGS is capable of forming a P1 helix with
      target sequence comprsing one or more uracil residues.
```

<400> SEQUENCE: 2
gacacgcggu uucugagcgc uuucagcacu ugagcgagga agggcgu            47

<210> SEQ ID NO 3
<211> LENGTH: 18
<212> TYPE: RNA
<213> ORGANISM: Artificial Sequence
<220> FEATURE:
<223> OTHER INFORMATION: Synthetic oligonucleotide comprising P10 Helix
      and AUG codon of a 3' exon of an exemplary trans-splicing intron
      targeting a Dengue Virus 2 RNA.
<220> FEATURE:
<221> NAME/KEY: misc_feature
<222> LOCATION: (5)..(10)
<223> OTHER INFORMATION: Region in an exemplary trans-splicing intron
      targeting a Dengue Virus 2 RNA is complementary to a portion of
      the Internal Guide Sequence (IGS) of the intron capable of forming
      a P10 helix.
<220> FEATURE:
<221> NAME/KEY: misc_feature
<222> LOCATION: (16)..(18)
<223> OTHER INFORMATION: AUG start codon in an exemplary trans-splicing
      intron targeting a Dengue Virus 2 RNA.

<400> SEQUENCE: 3
ucgauccucg agaccaug                                            18

<210> SEQ ID NO 4
<211> LENGTH: 166
<212> TYPE: RNA
<213> ORGANISM: Human immunodeficiency virus
<220> FEATURE:
<221> NAME/KEY: misc_feature
<222> LOCATION: (1)..(166)
<223> OTHER INFORMATION: Residues of an HIV RNA illustrated in Figure 4,
      corresponding to residues 206 to 371.

<400> SEQUENCE: 4
ccgccugguc auucggoguguu caccugagua acaagacccu ggccuguuag gacccuucuu    60 gcuuuqqqaa accgaggcag gaaaaucccu agcagguugg cgcccgaaca gggacuugaa   120
gaagacugag aagucuugga acacggcuga gugaaggcag uaaggg                   166

<210> SEQ ID NO 5
<211> LENGTH: 76
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: tRNA
<222> LOCATION: (1)..(76)
<223> OTHER INFORMATION: Sequence corresponding to tRNA-Lys3
      complementary to a portion of the 5' end of an HIV RNA, including
      an HIV Primer Activating Sequence (HIVPAS) and an HIV Primer
      Binding Sequence (HIVPBS).

<400> SEQUENCE: 5
gcccggauag cucagdcggd agagcaucag acuuuurauc ugagggdcca ggguucaagu     60
cccuguucgg gcgcca                                                    76

<210> SEQ ID NO 6
<211> LENGTH: 18
<212> TYPE: RNA
<213> ORGANISM: Human immunodeficiency virus type 2
<220> FEATURE:
<221> NAME/KEY: misc_feature
<222> LOCATION: (1)..(18)

<223> OTHER INFORMATION: Region corresponding to nucleotides 303-320 in
      Figure 4 of an HIV RNA comprising an HIV Primer Binding Sequence
      (HIVPBS).

<400> SEQUENCE: 6
uggcgcccga acagggac                                                    18

<210> SEQ ID NO 7
<211> LENGTH: 18
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(18)
<223> OTHER INFORMATION: Region in a tRNA-Lys3 complementary to the HIV
      Primer Binding Sequence (HIVPBS).

<400> SEQUENCE: 7
gucccuguuc gggcgcca                                                    18

<210> SEQ ID NO 8
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: Experimental and Expected Splice Junctions for
      trans-splicing intron targeting U126 in HIV RNA comprising HIV
      sequences, intergenic region, and ATG start codon of 3' exon,
      illustrated in Figure 6.

<400> SEQUENCE: 8
ctgttgtgtg acttgcattc tgcatggtca tag                                   33

<210> SEQ ID NO 9
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(34)
<223> OTHER INFORMATION: Experimental and Expected Splice Junctions for
      trans-splicing intron targeting U128 in HIV RNA comprising HIV
      sequences, intergenic region, and ATG start codon of 3' exon,
      illustrated in Figure 6.

<400> SEQUENCE: 9
ctgttgtgtg actctggttg gaactcatgg tcat                                  34

<210> SEQ ID NO 10
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: Experimental and Expected Splice Junctions for
      trans-splicing intron targeting U182 in HIV RNA comprising HIV
      sequences, intergenic region, and ATG start codon of 3' exon,
      illustrated in Figure 6.

<400> SEQUENCE: 10
aaatctctag cagtgtcgtg accacatggt cat                                      33

<210> SEQ ID NO 11
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(34)
<223> OTHER INFORMATION: Expected Splice Junction for trans-splicing
      intron targeting U128 with an EGS targeting the HIVPBS in HIV RNA
      comprising HIV sequences, intergenic region, and ATG start codon
      of 3' exon, illustrated in Figure 6.

<400> SEQUENCE: 11
ctgttgtgtg actctgcttg gcattgcatg gtca                                     34

<210> SEQ ID NO 12
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: Experimental Splice Junction for trans-splicing
      intron targeting U128 with an EGS targeting the HIVPBS in HIV RNA
      comprising HIV sequences, intergenic region, and ATG start codon
      of 3' exon, illustrated in Figure 6.

<400> SEQUENCE: 12
ctgttgtgtg actctgcttg ccattcatgg tca                                      33

<210> SEQ ID NO 13
<211> LENGTH: 8
<212> TYPE: RNA
<213> ORGANISM: Human immunodeficiency virus
<220> FEATURE:
<221> NAME/KEY: misc_feature
<222> LOCATION: (1)..(9)
<223> OTHER INFORMATION: 9 nt target region designated HIVPAS
      (corresponding to nt 577 to 584 of prototype strain HIV HBX2, or
      nt 123 to 130 of Beerens and Berkhout) which has affinity to IGS
      region of trans-splicing intron

<400> SEQUENCE: 13 gacucugg                                                                   8

<210> SEQ ID NO 14
<211> LENGTH: 18
<212> TYPE: RNA
<213> ORGANISM: Human immunodeficiency virus
<220> FEATURE:
<221> NAME/KEY: misc_feature
<222> LOCATION: (1)..(18)
<223> OTHER INFORMATION: HIV Primer Binding Site (HIVPBS)

<400> SEQUENCE: 14
uggcgcccga acagggac                                                       18

<210> SEQ ID NO 15
<211> LENGTH: 9
<212> TYPE: RNA
<213> ORGANISM: Artificial Sequence
<220> FEATURE:
<223> OTHER INFORMATION: Synthetic Internal Guide Sequence (IGS), part

```
of a trans-splicing intron partially complementary to and
targeting uracil position U126 corresponding to nucleotide 4 in
the HIVPAS sequence 5'-GACUCUGG-3' in HIV RNAs.
<220> FEATURE:
<221> NAME/KEY: misc_feature
<222> LOCATION: (1)..(9)
<223> OTHER INFORMATION: Synthetic Internal Guide Sequence (IGS), part
      of a trans-splicing intron partially complementary to and
      targeting uracil position U126 corresponding to nucleotide 4 in
      the HIVPAS sequence 5'-GACUCUGG-3' in HIV RNAs.

<400> SEQUENCE: 15 cagggucac                                                                 9

<210> SEQ ID NO 16
<211> LENGTH: 9
<212> TYPE: RNA
<213> ORGANISM: Artificial Sequence
<220> FEATURE:
<223> OTHER INFORMATION: Synthetic Synthetic Internal Guide Sequence
      (IGS), part of a trans-splicing intron partially complementary to
      and targeting uracil position U128 corresponding to nucleotide 6
      in the HIVPAS sequence 5'-GACUCUGG-3' in HIV RNAs.
<220> FEATURE:
<221> NAME/KEY: misc_feature
<222> LOCATION: (1)..(9)
<223> OTHER INFORMATION: Synthetic Internal Guide Sequence (IGS), part
      of a trans-splicing intron partially complementary to and
      targeting uracil position U128 corresponding to nucleotide 6 in
      the HIVPAS sequence 5'-GACUCUGG-3' in HIV RNAs.

<400> SEQUENCE: 16 accggaguc                                                                 9

<210> SEQ ID NO 17
<211> LENGTH: 9
<212> TYPE: RNA
<213> ORGANISM: Artificial Sequence
<220> FEATURE:
<223> OTHER INFORMATION: Synthetic Internal Guide Sequence (IGS), part
      of a trans-splicing intron partially complementary to and
      targeting uracil position U182 corresponding to nucleotide 1 in
      the HIVPBS sequence 5'-GACUCUGG-3' in HIV RNAs.

<400> SEQUENCE: 17 gccgcugcu                                                                 9
```

What is claimed is:

1. An antiviral molecule comprising an anti-HIV-Group 1 (αHIV-Grp1) trans-splicing intron targeting one or more uracils within the HIV Primer Signal (HIVPAS) or the HIV primer binding site (HIVPBS) of any HIV target RNA, wherein said antiviral molecule comprises the following nucleic acid sequences in a 5' to 3' order:

(a) an External Guide Sequence (EGS) complementary to a segment of the target RNA downstream in a 3' direction from the target uracil;

(b) an Internal Guide Sequence (IGS) at least 9 nucleotides in length that is partially complementary to and capable of forming a P1 helix with a sequence comprising one or more uracils of the HIVPAS or HIVPBS target sequence;

wherein said P1 Helix comprises a G residue at position 4 of the IGS paired to a U residue of the target sequence, and each nucleotide residue of the IGS in the P1 helix flanking the G•U pair is complementary to a corresponding nucleotide residue in the target sequence;

(c) a nucleic acid sequence comprising a catalytic domain of a Group 1 trans-splicing intron; and (d) a nucleic acid sequence comprising an exon encoding a polypeptide capable of inducing apoptosis in a cell;

wherein said nucleic acid sequence (c) comprising a catalytic domain of a Group 1 trans-splicing intron is linked to said nucleic acid sequence (d) comprising an exon encoding a polypeptide capable of inducing apoptosis in a cell by the RNA equivalent of a nucleotide sequence selected from the group consisting of:

(i) 5'-TGCATTCTGC-3' (corresponding to residues 14 to 23 of SEQ ID NO: 8);

(ii) 5'-GGTTGGAACTC-3' (corresponding to residues 16 to 26 of SEQ ID NO: 9);

(iii) 5'-GCTTGGCATTGC-3' (corresponding to residues 16 to 27 of SEQ ID NO: 11);

(iv) 5'-GCTTGCCATTC-3' (corresponding to residues 16 to 26 of SEQ ID NO: 12); and (v) 5'-GTCGTGACCAC-3' (corresponding to residues 15 to 25 of SEQ ID NO: 10).

2. The antiviral molecule of claim 1, wherein the intron targets a uracil selected from the following positions:

(a) uracil position U 126 within the HIV Primer Activation Signal (HIVPAS), corresponding to nucleotide 4 within the sequence 5'-GACUCUGG-3' (SEQ ID NO: 13), wherein said IGS has the sequence 5'-CAGGGUCAC-3' (SEQ ID NO: 15), which is complementary to the HIVPAS at 6 of 8 positions;

(b) uracil position U 128 within the HIV Primer Activation Signal (HIVPAS), corresponding to nucleotide 6 within the sequence 5'-GACUCUGG-3' (SEQ ID NO: 13), wherein said IGS has the sequence 5'-ACCGGAGUC-3' (SEQ ID NO: 16), which is complementary to the HIVPAS at 7 of 8 positions; and (c) uracil position U 182 within the HIV primer binding site (HIVPBS), corresponding to nucleotide 1 within the sequence 5'-UGGCGCCCGAACAGGGAC-3' (SEQ ID NO: 14), wherein said IGS has the sequence 5'-GCCGCUGCU-3' (SEQ ID NO: 17), which is complementary to the HIVPBS at 3 of 4 positions.

3. A vector comprising a promoter operably-linked to a nucleotide sequence encoding the antiviral molecule of claim 1, wherein said vector is capable of transforming a population of cells to produce transformed cells that constitutively express said αHIV-Grp1 trans-splicing intron under the control of said operably-linked promoter.

4. The vector of claim 3, wherein said vector is a retroviral vector comprising a 5' retroviral Long Terminal Repeat (LTR), a retroviral ψ-packaging signal, a nucleotide sequence encoding a selectable marker operably-linked to a promoter, and a 3' retroviral LTR, wherein said 5' LTR and 3' LTR flank the retroviral packaging signal, wherein each of said operably-linked promoters are active in said transformed cells.

5. The retroviral vector of claim 4, wherein said promoter operably-linked to the nucleotide sequence encoding the antiviral molecule, is a CMV promoter.

6. A nucleic acid molecule encoding the antiviral molecule of claim 1.

7. The nucleic acid of claim 6, wherein said αHIV-Grp1 intron is selected from the group consisting of
(a) an intron, designated a PAS126 intron, targeting nucleotide 4 within the HIVPAS sequence 5'-GACUCUGG-3' (SEQ ID NO: 13);
(b) an intron, designated a PAS128 intron, targeting nucleotide 6 within the HIVPAS sequence 5'-GACUCUGG-3' (SEQ ID NO: 13); and
(c) an intron, designated a PBS182 intron, targeting nucleotide 1 within the (HIVPBS) sequence 5'-UGGCGCCCGAACAGGGAC-3' (SEQ ID NO: 14).

8. A nucleic acid encoding an anti-HIV-Group 1 (αHIV-Grp1) trans-splicing intron targeting one or more uracils within the HIV Primer Signal (HIVPAS) or the HIV primer binding site (HIVPBS) of any HIV target RNA, comprising the following nucleic acid sequences in a 5' to 3' order:

(a) an External Guide Sequence (EGS) complementary to a segment of the target RNA downstream in a 3' direction from the target uracil;

(b) an Internal Guide Sequence (IGS) at least 9 nucleotides in length that is partially complementary to and capable of forming a P1 helix with a sequence comprising one or more uracils of the HIVPAS or HIVPBS target sequence;
wherein said P1 Helix comprises a G residue at position 4 of the IGS paired to a U residue of the target sequence, and each nucleotide residue of the IGS in the P1 helix flanking the G•U pair is complementary to a corresponding nucleotide residue in the target sequence;

(c) a nucleic acid sequence comprising a catalytic domain of a Group 1 trans-splicing intron; and (d) a nucleic acid sequence comprising an exon encoding a polypeptide capable of inducing apoptosis in a cell;
wherein said nucleic acid sequence (c) comprising a catalytic domain of a Group 1 trans-splicing intron is linked to said nucleic acid sequence (d) comprising an exon encoding a polypeptide capable of inducing apoptosis in a cell by a nucleotide sequence selected from the group consisting of:
(i) 5'-TGCATTCTGC-3' (corresponding to residues 14 to 23 of SEQ ID NO: 8);
(ii) 5'-GGTTGGAACTC-3' (corresponding to residues 16 to 26 of SEQ ID NO: 9);
(iii) 5'-GCTTGGCATTGC-3' (corresponding to residues 16 to 27 of SEQ ID NO: 11);
(iv) 5'-GCTTGCCATTC-3' (corresponding to residues 16 to 26 of SEQ ID NO: 12); and
(v) 5'-GTCGTGACCAC-3' (corresponding to residues 15 to 25 of SEQ ID NO: 10);
wherein said αHIV-Grp1 intron is selected from the group consisting of
(i) an intron, designated a LOOP126 intron, targeting nucleotide 4 within the HIVPAS sequence 5'-GACUCUGG-3' (SEQ ID NO: 13), and said EGS is complementary to the HIV Primer Binding Site (HIVPBS); and
(ii) an intron, designated a LOOP 128 intron, targeting nucleotide 6 within the HIVPAS sequence 5'-GACUCUGG-3' (SEQ ID NO: 13), and said EGS is complementary to the HIV Primer Binding Site (HIVPBS).

9. The nucleic acid of claim 6, wherein said polypeptide capable of inducing apoptosis in a cell is a cysteine-dependent aspartate-specific protease.

10. The nucleic acid of claim 9, wherein said cysteine-dependent aspartate-specific protease is a caspase.

11. The nucleic acid of claim 6, wherein said polypeptide capable of inducing apoptosis in a cell is the proapoptotic pore-forming protein Bax, or derivatives thereof.

12. A vector comprising the nucleic acid encoding an αHIV-Grp1 intron of claim 6.

13. The vector of claim 12, further comprising a promoter that is functional in a mammalian cell, operably-linked to said intron.

14. The vector of claim 13, wherein said nucleic acid comprising said intron and said operably-linked promoter is capable of being stably-integrated into the genome of a mammalian cell.

15. A vector comprising the nucleic acid encoding an αHIV-Grp1 intron of claim 7.

16. The vector comprising the nucleic acid encoding an αHIV-Grp1 intron of claim 15, further comprising a promoter that is functional in a mammalian cell, operably-linked to said intron.

17. The vector of claim 16, wherein said nucleic acid comprising said intron and said operably-linked promoter is capable of being stably-integrated into the genome of a mammalian cell.

18. A vector comprising the nucleic acid encoding an αHIV-Grp1 intron of claim 8.

19. The vector of claim 18, further comprising a promoter that is functional in a mammalian cell, operably-linked to said intron.

20. The vector of claim 19, wherein said nucleic acid comprising said intron and said operably-linked promoter is capable of being stably-integrated into the genome of a mammalian cell.

21. The nucleic acid of claim 8, wherein said polypeptide capable of inducing apoptosis in a cell is a cysteine-dependent aspartate-specific protease.

22. The nucleic acid of claim 21, wherein said cysteine-dependent aspartate-specific protease is a caspase.

23. The nucleic acid of claim 8, wherein said polypeptide capable of inducing apoptosis in a cell is the proapoptotic pore-forming protein Bax, or derivatives thereof.

24. An antiviral molecule of claim 1, wherein said αHIV-Grp1 trans-splicing intron targets one or more uracils within the HIV Primer Signal (HIVPAS) of any HIV target RNA.

* * * *

UNITED STATES PATENT AND TRADEMARK OFFICE
CERTIFICATE OF CORRECTION

PATENT NO. : 9,707,257 B2
APPLICATION NO. : 13/096626
DATED : July 18, 2017
INVENTOR(S) : Malcolm J. Fraser et al.

It is certified that error appears in the above-identified patent and that said Letters Patent is hereby corrected as shown below:

In the Specification

At Column 1, Lines 6-8, please delete:
"The United States federal government owns rights in the present technology as research was supported by funds from National Institutes of Health Grant #777."

And insert:
-- This invention was made with government support under grant R01 AI097554 awarded by the National Institutes of Health. The government has certain rights in the invention. -- therefor.

Signed and Sealed this
Nineteenth Day of July, 2022

Katherine Kelly Vidal
*Director of the United States Patent and Trademark Office*